(12) United States Patent
Herschkowitz et al.

(10) Patent No.: US 9,375,530 B2
(45) Date of Patent: Jun. 28, 2016

(54) METHODS AND DEVICES FOR DESMOPRESSIN DRUG DELIVERY

(71) Applicant: Allergan, Inc., Irvine, CA (US)

(72) Inventors: Samuel Herschkowitz, Brooklyn, NY (US); Seymour H. Fein, New Canann, CT (US)

(73) Assignee: Allergan, Inc., Irvine, CA (US)

( * ) Notice: Subject to any disclaimer, the term of this patent is extended or adjusted under 35 U.S.C. 154(b) by 378 days.

(21) Appl. No.: 13/768,510

(22) Filed: Feb. 15, 2013

(65) Prior Publication Data

US 2014/0058313 A1 Feb. 27, 2014

Related U.S. Application Data

(62) Division of application No. 12/186,886, filed on Aug. 6, 2008, now Pat. No. 8,399,410.

(60) Provisional application No. 60/954,159, filed on Aug. 6, 2007.

(51) Int. Cl.
| | |
|---|---|
| *A61K 38/08* | (2006.01) |
| *A61M 5/145* | (2006.01) |
| *A61M 5/172* | (2006.01) |
| *A61M 5/175* | (2006.01) |
| *A61M 5/48* | (2006.01) |
| *A61M 5/168* | (2006.01) |
| *A61M 37/00* | (2006.01) |
| *A61M 35/00* | (2006.01) |
| *A61N 1/30* | (2006.01) |

(52) U.S. Cl.
CPC ............. *A61M 5/168* (2013.01); *A61K 38/08* (2013.01); *A61M 5/482* (2013.01); *A61M 35/00* (2013.01); *A61M 37/0015* (2013.01); *A61M 37/0092* (2013.01); *A61N 1/30* (2013.01)

(58) Field of Classification Search
None
See application file for complete search history.

(56) References Cited

U.S. PATENT DOCUMENTS

| | | | |
|---|---|---|---|
| 3,989,816 | A | 11/1976 | Rajadhyaksha |
| 4,263,283 | A | 4/1981 | Cort |
| 4,285,858 | A | 8/1981 | Cort et al. |

(Continued)

FOREIGN PATENT DOCUMENTS

| | | |
|---|---|---|
| EP | 0278474 A1 | 8/1988 |
| WO | WO-9501183 A1 | 1/1995 |

(Continued)

OTHER PUBLICATIONS

Cormier et al. (2004) "Transdermal delivery of desmopressin using a coated microneedle array patch system," *Journal of Controlled Release* 97:503-511.

(Continued)

*Primary Examiner* — Jeffrey E Russel
(74) *Attorney, Agent, or Firm* — Brigitte C. Phan; Ted A. Chan

(57) ABSTRACT

Disclosed are devices for urine voiding postponement, and methods for treating conditions such as central diabetes insipidus, enuresis, nocturia, urinary frequency or incontinence. The devices deliver a desmopressin flux through the skin of a patient in a low dose amount just necessary to achieve a desired anti-diuretic effect without undesirable side effects such as hyponatremia. The devices are designed to permit a state of normal urinary production to return quickly after the desmopressin flux is terminated.

18 Claims, 7 Drawing Sheets

(56) References Cited

U.S. PATENT DOCUMENTS

| | | |
|---|---|---|
| 4,316,893 A | 2/1982 | Rajadhyaksha |
| 4,405,616 A | 9/1983 | Rajadhyaksha |
| 4,557,934 A | 12/1985 | Cooper |
| 4,588,580 A | 5/1986 | Gale et al. |
| 4,698,062 A * | 10/1987 | Gale ............... A61M 35/00 424/449 |
| 4,783,450 A | 11/1988 | Fawzi et al. |
| 4,863,737 A | 9/1989 | Stanley et al. |
| 4,878,892 A | 11/1989 | Sibalis et al. |
| 5,032,109 A | 7/1991 | Sibalis |
| 5,047,398 A | 9/1991 | Hagstam et al. |
| 5,091,186 A | 2/1992 | Miranda et al. |
| 5,135,480 A | 8/1992 | Bannon et al. |
| 5,298,256 A | 3/1994 | Flockhart et al. |
| 5,441,490 A | 8/1995 | Svedman et al. |
| 5,464,387 A | 11/1995 | Haak et al. |
| 5,482,931 A | 1/1996 | Harris et al. |
| 5,498,598 A | 3/1996 | Harris |
| 5,500,413 A | 3/1996 | Larsson et al. |
| 5,527,288 A | 6/1996 | Gross et al. |
| 5,534,496 A | 7/1996 | Lee et al. |
| 5,596,078 A | 1/1997 | Andersson et al. |
| 5,611,806 A | 3/1997 | Jang et al. |
| 5,613,958 A | 3/1997 | Kochinke et al. |
| 5,631,246 A | 5/1997 | Hashemi et al. |
| 5,674,850 A | 10/1997 | Larsson et al. |
| 5,698,516 A | 12/1997 | Nilsson et al. |
| 5,707,648 A | 1/1998 | Yiv |
| 5,726,287 A | 3/1998 | Andersson et al. |
| 5,763,398 A | 6/1998 | Bengtsson et al. |
| 5,763,405 A | 6/1998 | Fjellestad-Paulsen et al. |
| 5,763,407 A | 6/1998 | Larsson et al. |
| 5,780,434 A | 7/1998 | Fjellestad-Paulsen |
| 5,840,899 A | 11/1998 | Bedeschi et al. |
| 5,843,016 A | 12/1998 | Lugnani et al. |
| 5,843,114 A | 12/1998 | Jang et al. |
| 5,848,991 A | 12/1998 | Gross et al. |
| 5,879,326 A | 3/1999 | Godshall et al. |
| 5,906,831 A | 5/1999 | Larsson et al. |
| 5,922,680 A | 7/1999 | Fjellestad-Paulsen et al. |
| 5,932,745 A | 8/1999 | Dushin et al. |
| 5,948,433 A | 9/1999 | Burton et al. |
| 5,985,385 A | 11/1999 | Gottfried |
| 5,985,835 A | 11/1999 | Larsson et al. |
| 5,990,273 A | 11/1999 | Andersson et al. |
| 6,010,478 A | 1/2000 | Bellhouse et al. |
| 6,090,803 A | 7/2000 | Failli et al. |
| 6,139,866 A | 10/2000 | Chono et al. |
| 6,143,722 A | 11/2000 | Melin et al. |
| 6,148,232 A | 11/2000 | Avrahami et al. |
| 6,194,407 B1 | 2/2001 | Failli et al. |
| 6,235,900 B1 | 5/2001 | Failli et al. |
| 6,248,363 B1 | 6/2001 | Patel et al. |
| 6,268,360 B1 | 7/2001 | Failli et al. |
| 6,297,234 B1 | 10/2001 | Failli et al. |
| 6,314,317 B1 | 11/2001 | Willis |
| 6,322,532 B1 | 11/2001 | D'Sa et al. |
| 6,344,451 B1 | 2/2002 | Steffan et al. |
| 6,348,486 B1 | 2/2002 | Argentieri et al. |
| 6,406,455 B1 | 6/2002 | Willis et al. |
| 6,490,483 B2 | 12/2002 | Willis |
| 6,511,974 B1 | 1/2003 | Dusza et al. |
| 6,558,695 B2 | 5/2003 | Luo et al. |
| 6,564,093 B1 | 5/2003 | Ostrow et al. |
| 6,616,627 B2 | 9/2003 | Willis et al. |
| 6,620,807 B1 | 9/2003 | Steffan et al. |
| 6,664,249 B1 | 12/2003 | Ashworth et al. |
| 6,693,082 B2 | 2/2004 | Alonso et al. |
| 6,720,001 B2 | 4/2004 | Chen et al. |
| 6,723,077 B2 | 4/2004 | Pickup et al. |
| 6,746,678 B1 | 6/2004 | Shapiro |
| 6,893,655 B2 | 5/2005 | Flanigan et al. |
| 6,903,091 B2 | 6/2005 | Failli et al. |
| 6,930,932 B2 | 8/2005 | Rentschler |
| 6,939,324 B2 | 9/2005 | Gonnelli et al. |
| 6,945,952 B2 | 9/2005 | Kwon |
| 6,960,184 B2 | 11/2005 | Willis et al. |
| 7,018,653 B2 | 3/2006 | Wannerberger et al. |
| 7,022,340 B2 | 4/2006 | Lomryd et al. |
| 7,022,699 B2 | 4/2006 | Failli et al. |
| 7,027,478 B2 | 4/2006 | Ackley |
| 7,053,083 B2 | 5/2006 | Failli et al. |
| 7,060,708 B2 | 6/2006 | Piccariello et al. |
| 7,074,781 B2 | 7/2006 | Ashworth et al. |
| 7,090,763 B2 | 8/2006 | Gottschling et al. |
| 7,094,545 B2 | 8/2006 | Lomryd et al. |
| 7,097,631 B2 | 8/2006 | Trautman et al. |
| 7,097,776 B2 | 8/2006 | Govinda Raju et al. |
| 7,138,393 B2 | 11/2006 | Molinari et al. |
| 7,150,409 B2 | 12/2006 | Gonnelli et al. |
| 7,153,845 B2 | 12/2006 | Levine et al. |
| 7,180,274 B2 | 2/2007 | Chen et al. |
| 7,182,747 B2 | 2/2007 | Kwon |
| 7,187,969 B2 | 3/2007 | Willis |
| 7,383,084 B2 | 6/2008 | Stern et al. |
| 7,405,203 B2 | 7/2008 | Fein |
| 7,579,321 B2 | 8/2009 | Fein |
| 7,799,761 B2 | 9/2010 | Fein |
| 8,143,225 B2 | 3/2012 | Fein |
| 8,399,410 B2 * | 3/2013 | Herschkowitz et al. ..... 514/10.9 |
| 2002/0013262 A1 | 1/2002 | Alonso et al. |
| 2002/0016562 A1 | 2/2002 | Cormier et al. |
| 2002/0082543 A1 | 6/2002 | Park et al. |
| 2002/0107265 A1 | 8/2002 | Chen et al. |
| 2002/0128599 A1 | 9/2002 | Cormier et al. |
| 2002/0178196 A1 | 11/2002 | Monier |
| 2002/0198191 A1 | 12/2002 | Failli et al. |
| 2003/0018024 A1 | 1/2003 | Failli et al. |
| 2003/0054044 A1 | 3/2003 | Potter et al. |
| 2003/0087892 A1 | 5/2003 | Ashworth et al. |
| 2003/0119728 A1 | 6/2003 | Scheidl et al. |
| 2003/0134845 A1 | 7/2003 | Molinari et al. |
| 2004/0018241 A1 | 1/2004 | Houze et al. |
| 2004/0038962 A1 | 2/2004 | Ashworth et al. |
| 2004/0063628 A1 | 4/2004 | Piccariello et al. |
| 2004/0115167 A1 | 6/2004 | Cormier et al. |
| 2004/0138098 A1 | 7/2004 | Fein |
| 2004/0138610 A1 | 7/2004 | Cormier et al. |
| 2004/0220080 A1 | 11/2004 | Lomryd et al. |
| 2004/0242686 A1 | 12/2004 | Isawa et al. |
| 2004/0249339 A1 | 12/2004 | Willis et al. |
| 2004/0265365 A1 | 12/2004 | Daddona et al. |
| 2005/0004103 A1 | 1/2005 | Koshio et al. |
| 2005/0019392 A1 | 1/2005 | Lomryd et al. |
| 2005/0075328 A1 | 4/2005 | Failli et al. |
| 2005/0089554 A1 | 4/2005 | Cormier et al. |
| 2005/0096586 A1 | 5/2005 | Trautman et al. |
| 2005/0106226 A1 | 5/2005 | Cormier et al. |
| 2005/0153873 A1 | 7/2005 | Chan et al. |
| 2005/0154350 A1 | 7/2005 | Willis et al. |
| 2005/0158378 A1 | 7/2005 | Wannerberger et al. |
| 2005/0232997 A1 | 10/2005 | Nilsson et al. |
| 2006/0025387 A1 | 2/2006 | Hochman |
| 2006/0040970 A1 | 2/2006 | Izumimoto et al. |
| 2006/0060106 A1 | 3/2006 | Ueda |
| 2006/0093658 A1 | 5/2006 | Sathyan et al. |
| 2006/0122113 A1 | 6/2006 | Pinchasi et al. |
| 2006/0122170 A1 | 6/2006 | Koshio et al. |
| 2006/0138719 A1 | 6/2006 | Petit et al. |
| 2006/0154916 A1 | 7/2006 | Ashworth et al. |
| 2006/0161111 A1 | 7/2006 | Potter et al. |
| 2006/0183734 A1 | 8/2006 | Failli et al. |
| 2006/0189939 A1 | 8/2006 | Gonnelli et al. |
| 2006/0193825 A1 | 8/2006 | Musso et al. |
| 2006/0200069 A1 | 9/2006 | Cormier et al. |
| 2006/0233871 A1 | 10/2006 | Stern et al. |
| 2006/0240068 A1 | 10/2006 | Lomryd et al. |
| 2006/0241172 A1 | 10/2006 | Zhou et al. |
| 2006/0241176 A1 | 10/2006 | Stack et al. |
| 2006/0247276 A1 | 11/2006 | Gross et al. |
| 2006/0252696 A1 | 11/2006 | Lomryd et al. |
| 2006/0253061 A1 | 11/2006 | Anderson et al. |
| 2006/0258712 A1 | 11/2006 | Jacobson |
| 2006/0258714 A1 | 11/2006 | Heffernan et al. |

(56) References Cited

U.S. PATENT DOCUMENTS

| | | | |
|---|---|---|---|
| 2006/0258739 | A1 | 11/2006 | Ai et al. |
| 2007/0002523 | A1 | 1/2007 | Ando et al. |
| 2007/0027427 | A1 | 2/2007 | Trautman et al. |
| 2007/0032410 | A1 | 2/2007 | Quay et al. |
| 2007/0127976 | A1 | 6/2007 | Murakoshi |
| 2007/0265207 | A1 | 11/2007 | Fein |
| 2008/0274951 | A1 | 11/2008 | Fein |
| 2009/0005432 | A1 | 1/2009 | Fein |
| 2009/0042970 | A1 | 2/2009 | Herschkowitz et al. |
| 2010/0056436 | A1 | 3/2010 | Fein |
| 2010/0160214 | A1 | 6/2010 | Fein et al. |
| 2012/0015880 | A1 | 1/2012 | Fein |

FOREIGN PATENT DOCUMENTS

| | | |
|---|---|---|
| WO | WO-02/064193 A2 | 8/2002 |
| WO | WO-02/074286 | 9/2002 |
| WO | WO-02094368 | 11/2002 |
| WO | WO-03/094885 | 11/2003 |
| WO | WO-03094886 | 11/2003 |
| WO | WO-2004/041153 A2 | 5/2004 |
| WO | WO-2005041871 A2 | 5/2005 |
| WO | WO-2005046707 A1 | 5/2005 |
| WO | WO-2006060106 A1 | 6/2006 |
| WO | WO-2006085101 A2 | 8/2006 |
| WO | WO-2006138719 A2 | 12/2006 |
| WO | WO-2007002523 A2 | 1/2007 |
| WO | WO-2007083323 A2 | 7/2007 |
| WO | WO-2007127976 A2 | 11/2007 |
| WO | WO-2009021007 A1 | 2/2009 |
| WO | WO-2010/075266 A2 | 7/2010 |
| WO | WO-2010/147981 A1 | 12/2010 |

OTHER PUBLICATIONS

Gill et al. (2007) "Coated microneedles for transdermal delivery," *J. Control Release* 117(2):227-237.
Kwon. (2004) "In vitro evaluation of transdermal drug delivery by a micro-needle patch," *Controlled Release Society 31st Annual Meeting Transactions*, #115.
Kwon. (2007) "Dissolvable microneedle patch for biopharmaceuticals delivery and vaccination," *Drug Delivery Report* Winter 2007/2008:56-57.
Meyer et al. (1988) "Successful transdermal administration of therapeutic doses of a polypeptide to normal human volunteers," *Clin. Pharmacol. & Therapeutics* 44(6):607-612.
Meyer et al. (1990) "Transdermal versus subcutaneous leuprolide: a comparison of acute pharmacodynamic effect," *Clin. Pharmacol. & Therapeutics* 48(4):340-5.
Pai-Thakur et al. (2007) "Technology Update: Minimally Invasive Injections: Dream or Reality?" *American Association of Indian Pharmaceutical Scientists* 17(4): 9-10.
Park et al. (2006) "Polymer microneedles for controlled-release drug delivery," *Pharm. Res.* 23(5):1008-1019.
Svedman et al. (1991) "Administration of antidiuretic peptide (DDAVP) by way of suction de-epithelialized skin," *The Lancet* 337:1506-1509.
Wermeling et al. (2008) "Microneedles permit transdermal delivery of a skin-impermeant medication to humans," *PNAS* 105(6):2058-2063.
Doctoral Dissertation, "Absorption and Metabolism of Neurohypophyseal Hormones, with special reference to Desmopressin (dDAVP), in Human Tissue and after Various Routes of Administration", (Fjellestad-Paulsen, Anne M.) May 25, 1996.
Trinh-Trang-Tan et al. "Regulation of UT-A2 Protein in vivo and in vitro", *Journal of the American Society of Nephrology*, (Sep. 2000) vol. 11, No. Program and Abstract Issue, pp. 23A.
Wolfson et al. (1979) "Mechanism of Vasopressin Inhibition of Pancreatic Secretion," *American Journal of Gastroenterology*, vol. 71, No. 5, pp. 490-495.
Jahr et al. (1992) "Effect of Desmopressin Acetate on Hindlimb Perfusion Pressure in Rats: What is the Mechanism?" *Anesthesia & Analgesia*, vol. 75, No. 3, pp. 411-415.
Dixon et al. (1981) "The Effect of DDAVP on Intravenous Urography", *British Journal of Radiology*, vol. 54, pp. 484-487.
Malan et al. (1994) "Subcutaneous Administration of Desmopressin as a Test of Maximal Urinary Concentrating Ability in the Fischer 344 Rat", *Toxicology Methods*, vol. 4, No. 3, pp. 188-192.
Tormey & O'Laoire (1992) "Severe Prolonged Antidiuresis Following Desmopressin and Carbamazepine Interaction in Postoperative Diabetes Insipidus," *European Journal of Internal Medicine*, vol. 3, pp. 341-343.
Patent Cooperation Treaty (PCT) International Search Report; International Application No. PCT/US03/14463, mailed on May 27, 2004.
Patent Cooperation Treaty (PCT) International Search Report; International Application No. PCT/US03/35662, mailed on Sep. 30, 2004.
Vilhardt et al. (1986) "Plasma Kinetics of DDAVP in Man," *Acta Pharmacol Toxicol (Copenh)*, 58 (5): 379-381.
"Minirin Nasal Spray". Ferring Pharmaceuticals. Internet document <<http://www.medsafe.gov.nz/Consumers/CMI/m/MinirinNSpray.htm>&g-t;, May 3, 2001; accessed Oct. 4, 2007; 3 pages.
"FDA Notice: Information for Healthcare Professionals Desmopressin Acetate (marketed as DDAVP Nasal Spray, DDAVP Rhinal Tube, DDAVP, DDVP, Minirin, and Stimate Nasal Spray)" available at http://www.fda.gov/cder/drug/InfoSheets/HCP/desmopressinHCP.htm (last visited Jan. 3, 2008).
Agnoli et al. (2002) "Low-dose desmopressin infusion: renal action in healthy women in moderate salt retention and depletion, and interactions with prostanoids," *Prostaglandins Leukotrienes and Essential Fatty Acids* 67(4): 263-273.
Grossman et al. (1980) "Two New Modes of Desmopressin (DDAVP) Administration," *British Medical Journal* 280(6225): 1215.
Janknegt et al. (1997) "Oral Desmopressin as a New Treatment Modality for Primary Nocturnal Enuresis in Adolescents and Adults: A Double-Blind, Randomized, Multicenter Study," *Journal of Urology* 157(2): 513-517.
Supplementary European Search Report (2008) for European Application No. EP03781836 (4 pages).
Robinson (1976) "DDAVP in the Treatment of Central Diabetes Insipidus," *N Engl J Med* 294: 507-511.
Swain (1999) "Blister Packaging Leads the Way: Despite continous pressure to contain costs, the demand for pharmaceutical packages keeps growing," *Pharma and Medical Packaging News Magazine* (4 pages).
Kohler et al. (1988) "Pharmacokinetics and haematological effects of desmopressin," *Eur J Clin Pharmacol* 35: 281-285.
Fjellestad-Paulsen et al., "Pharmacokinetics of 1-deamino-8-D-arginine vasopressin after various routes of administration in healthy volunteers," *Clinical Endocrinology* (1993) 38, pp. 177-182.
Kauli et al. (1985) "Treatment of Diabetes insipidus in Children and Adolescents," *Front. Horm. Res.* 13:304-313.
Olanoff et al. (1987) "Effect of intranasal histamine on nasal mucosal blood flow and the antidiuretic activity of desmopressin," *J Clin Invest.* 80(3):890-895.
"Drugs in Japan Ethical Drugs, Japan, Yakuji-Jihosha Incorporated (currently, Jiho Inc.), Oct. 15, 1999, 1192-1194," 13 pages.
"Desmopressin Spray 2.5 Kyowa, package insert, 2008, http://www.info.pmda.go.jp/downfiles/ph/PDF/231024_2419700R1022_1_10.pdf," 12 pages.
Fransén et al. (2009) "Clinical Study Shows Improved Absorption of Desmopressin with Novel Formulation," *Pharmaceutical Research*, 26(7):1618-1625.
Law et al. (2001) "Preparation of desmopressin-containing liposomes for intranasal delivery," *Journal of Controlled Release* 70:375-382.
Joukhadar et al. (2003) "A replicate study design for testing bioequivalence: a case study on two desmopressin nasal spray preparations," *Eur J Clin Pharmacol* 59: 631-636.
Request for *Ex Parte* Re-Examination of U.S. Pat. No. 7,405,203 filed Oct. 12, 2010, 42 pages.
Office Action issued in *Ex Parte* Re-Examination of U.S. Pat. No. 7,405,203, dated Nov. 10, 2010, 15 pages.

(56) References Cited

OTHER PUBLICATIONS

Desmopressin Acetate Package Insert for Desmopressin Injection: revised in Aug. 1998, Intranasal: revised in Jul. 1999, Spray: created in Oct. 1999; Drugs in Japan Ethical Drugs, Japan, Yakuji—Jihosha, Inc., (in Japanese; with English translation attached) 13 pages.
Fabrizio B., et al., (2009) "In vitro permeation of desmopressin across rabbit nasal mucosa from liquid nasal sprays: The enhancing effect of potassium sorbate," European Journal of Pharmaceutical Sciences, vol. 37, No. 1, pp. 36-42.
Patent Cooperation Treaty (PCT) International Search Report; International Application No. PCT/US2008/072290, mailed on Nov. 3, 2008 (4 pages).
Patent Cooperation Tready (PCT) International Preliminary Report on Patentability; International Application No. PCT/US2008/072290, issued on Feb. 9, 2010 (8 pages).
Patent Cooperation Treaty (PCT) International Search Report; International Application No. PCT/US2009/068962, mailed on Nov. 19, 2010 (4 pages).
Doctoral Dissertation, "Absorption and Metabolism of Neurophypophyseal Hormones, with special reference to Desmopressin (dDAVP), in Human Tissue and after Various Routes of Administration", (Fjellestad-Paulsen, Anne M.) May 25, 1996.
Wolfson Philip et al. (1979) "Mechanism of Vasopressin Inhibition of Pancreatic Secretion", American Journal of Gastroenterology, vol. 71, No. 5, pp. 490-495.
Jahr S Jonathan et al. (1992) "Effect of Desmopressin Acetate on Hindlimb Perfusion Pressure in Rats: What is the Mechanism?" Anesthesia & Analgesia, vol. 75, No. 3, pp. 441-445.
Dixon A.K. et al. (1981) "The Effect of DDAVP on Intravenous Urography", British Journal of Radiology, vol. 54, pp. 484-487.
Malan T. Philip et al. (1994) "Subcutaneous Administration of Desmopressin as a Test of Maximal Urinary Concentrating Ability in the Fischer 344 Rat", Toxicology Methods, vol. 4, No. 3, pp. 188-192.
Tormey William Patrick & O'Laoire Sean Arthur (1992) "Severe Prolonged Antidiuresis Following Desmopressin and Carbamazepine Interaction in Postoperative Diabetes Insipidus", European Journal of Internal Medicine, vol. 3, pp. 341-343.
Vilhardt H et al. (1986) "Plasma Kinetics of DDAVP in Man", Acta Pharmacol Toxicol (Copenh), 58 (5): 379-381.
Williams et al. (1986) "Antidiuretic Effect and Pharmacokinetics of Oral 1-Desamino-8-D-Arginine Vasopressin. 1. Studies in Adults and Children," *Journal of Clinical Endocrinology and Metabolism* 63:129-132.
Hammer and Vilhardt. (1985) "Peroral Treatment of Diabetes Insipidus with a Polypeptide Hormone Analog, Desmopressin," *The Journal of Pharmacology and Experimental Therapeutics*. 234:754-760.
Laczi et al. (1980) "Effects of vasopressin analogues (DDAVP, DVDAVP) in the form of sublingual tablets in central diabetes insipidus," *International Journal of Clinical Pharmacology, Therapy and Toxicology*. 12:63-68.
Nakakura et al. (1997) "Prolongation of antidiuretic response to desmopressin acetate by iontophoretic transdermal delivery in rats" Biol. Pharma. Bull. 20(5):537-540 (abstract only).
Search Report for Chinese Patent Application No. 200880107384 dated Jul. 25, 2012 (1 page).
Written Opinion for International Patent Application No. PCT/US2008/072290, dated Nov. 3, 2008 (7 pages).

* cited by examiner

METHODS AND DEVICES FOR DESMOPRESSIN DRUG DELIVERY

REFERENCE TO RELATED APPLICATION

This application is a divisional of U.S. application Ser. No. 12/186,886, filed Aug. 6, 2008, which claims priority to, and the benefit of, U.S. Application No. 60/954,159, filed Aug. 6, 2007, the complete disclosures of each of which being incorporated by reference herein for all purposes.

FIELD OF THE INVENTION

The invention relates to medical devices for voiding postponement, and methods for treating conditions characterized by overproduction of urine, e.g., diabetes insipidus; enuresis, nocturia, incontinence, frequency, or urgency.

BACKGROUND OF THE INVENTION

Desmopressin (1-desamino-8-D-arginine vasopressin, dDAVP®) is an analogue of vasopressin. Desmopressin has decreased vasopressor activity and increased anti-diuretic activity compared to vasopressin. This pharmacological profile enables desmopressin to be used clinically for anti-diuresis without causing significant increases in blood pressure. Desmopressin is commercially available as the acetate salt both in tablet form and as a nasal spray, and is commonly prescribed for primary nocturnal enuresis (PNE) and central diabetes insipidus. Commercially available dosage forms have not been approved for use to treat nocturia, voiding postponement, or incontinence.

Desmopressin has been administered intravenously, subcutaneously, intranasally, and orally. The intravenous route of administration is clinically used almost exclusively to treat patients with mild hemophilia or Von Willebrand's Disease to raise blood levels of Factor VIII prior to surgery. Subcutaneous injection is used infrequently and primarily in patients with central diabetes insipidus, a deficiency of endogenous vasopressin resulting in the renal production of large volumes of extremely dilute urine which can cause severe dehydration. Intranasal administration of desmopressin via a nasal spray is approved for the maintenance treatment of patients with central diabetes insipidus and in children (ages 6 to 16 years) with primary nocturnal enuresis. An oral tablet dosage form of desmopressin has also been approved for the treatment of central diabetes insipidus and primary nocturnal enuresis.

A major drawback of subcutaneous injection is that it is a difficult and uncomfortable procedure, resulting in poor patient compliance, especially in children. While oral or nasal routes of administration are more convenient they produce low and variable bioavailabilities of 0.1% for oral and 3.4% for nasal with 10 to 20 fold ranges for peak blood levels. Desmopressin, an 1183 Da molecule, is usually dosed at 10 to 20 micrograms (μg) for nasal and 100 to 400 μg for oral administration.

Currently, approved labeling for desmopressin recommends dosing in the following ranges depending on the clinical indication and the route of administration:

| Clinical Indication | Route of Administration (% Bioavailability) | Dose Range (daily) |
| --- | --- | --- |
| Hemophilia/Von Willebrand's | Intravenous (100) | 0.3 mcg/kg (21 mcg for 70 kg patients) |
| Central Diabetes Insipidus (CDI) | Intravenous (100) | 2-4 mcg qd or 1-2 mcg bid |
| | Subcutaneous (±90) | 2-4 mcg qd or 1-2 mcg bid |
| | Intranasal (3-5) | 5-40 mcg qd or 5-20 mcg bid |
| | Oral (0.1) | 100-600 mcg bid |
| Primary Nocturnal Enuresis (PNE) | Intranasal (3-5) | 10-40 mcg qhs |
| | Oral (0.1) | 200-600 mcg qhs |

The average maximum plasma/serum concentrations achieved ($C_{max}$) with a typical intranasal dose (20 μg, 10 μg in each nostril) of desmopressin for central diabetes insipidus (CDI) or PNE is approximately 20-30 pg/ml, based on 3-5% bioavailability. For the desmopressin oral tablet with only 0.1-0.15% bioavailability, a standard dose of 200-400 μg would also produce an average peak plasma/plasma/serum level of 20-30 pg/ml. (Bioavailability varies widely from person to person.)

While existing formulations of desmopressin have proven to be adequate for many patients when used for these clinical indications, variable efficacy and occasional hyponatremia continue to be problems related to the aforementioned variability. Tablets are often preferred by patients because of their ease of use, discretion and the lack of uncertainty of correct administration. However, tablets generally need to be taken with a glass of water or other drink, which is a problem, since fluid intake needs to be restricted in connection with desmopressin treatment; and the message to the patient is much clearer when there is no water intake at all. In addition, while the above doses and plasma/serum concentrations are effective for treating CDI and PNE, standard dosages of desmopressin have been shown to cause undesirable side-effects including high incidences of hyponatremia.

In fact, the U.S. Food & Drug Administration recently warned physicians and the public that "[c]ertain patients, including children treated with the intranasal formulation of [desmopressin acetate] for primary nocturnal enuresis (PNE), are at risk for developing severe hyponatremia that can result in seizures or death."

SUMMARY OF THE INVENTION

The present invention relates to methods and devices for administering desmopressin to reduce urine production for a predetermined, short period of time and, thereafter, to restore normal urine production. Accordingly, these methods and devices are useful in the treatment of conditions such as central diabetes insipidus, nocturnal enuresis, nocturia, urinary frequency and urinary incontinence. Desmopressin is administered to or across the skin of a patient at a level sufficient to achieve and maintain, for a selected, controllable and consistent period of time, an anti-diuretic effect which avoids undesirable side effects that include hyponatremia. In essence, the methods and devices act as an artificial organ, supplementing or replacing pituitary vasopressin secretion activity, but are controlled by the patient and his or her physician.

Because the duration of the anti-diuretic effect is known, or stated differently, because normal diuresis returns within about one-half to two hours after termination of the influx of the drug into the patient's blood stream, and the time of such termination is known, the risk is essentially eliminated that a patient will inadvertently consume aqueous liquids during the interval of anti-diuresis and develop hyponatremia.

The methods and devices described herein control the rate of administration of desmopressin to maintain a plasma/serum desmopressin concentration which is slightly above the threshold for anti-diuretic effect. In contrast to non-parenteral dosage forms of the prior art which are characterized not only by low bioavailability but also variable (both inter patient and intra patient) bioavailability, the devices of the invention have generally high (e.g. greater than 70%) bioavailability and, more important, a lower variation in bioavailability. The administration of a steady and controlled low dosage regime of desmopressin is intended to avoid undesirable side effects, including variable efficacy, water intoxication (hyponatremia), sleep disturbance and discomfort during the procedure. In accordance with the invention, maintenance of a consistent, slightly supra-threshold concentration of desmopressin in the blood through control of influx enables the prompt termination of anti-diuretic effect and restoration of normal urine production rapidly upon discontinuance of desmopressin flux. Accordingly, water channels in the kidneys of the patient can be activated or inactivated as desired, and urine production can be initiated or suppressed within a relatively short response time, with little effort and improved precision. The precision and quality of desmopressin treatment with the invention is further enhanced by the high and more consistent bioavailability of the drug due to its administration into or through the skin, as compared with oral, nasal, or buccal routes.

In one aspect, the invention provides methods of modulating urine production in a patient in need of such modulation, such as a patient suffering from diabetes insipidus, enuresis, nocturia, incontinence, or primary nocturnal enuresis (PNE). The methods include administering desmopressin to or across the skin of a patient, and can incorporate any of a variety of transdermal or intradermal administration methods. The desmopressin is administered at a rate or in an amount sufficient to establish a desmopressin concentration in the blood within the range of about 0.2 to 5 pg/ml (or, in some embodiments, within the range of 0.5 to 2.5 pg/ml) and insufficient to establish a higher concentration in the blood. The administered desmopressin reduces urine production in the patient. The methods include maintaining the desmopressin concentration in the blood within the range for a period of time, which may be at least about two hours (e.g. two to eight hours, four to seven hours, at least three hours, or no more than about three, four, five, six, seven, eight, nine, ten, or twelve hours). Because the concentration of desmopressin is maintained slightly above the efficacy threshold, terminating the administration permits the reestablishment of urine production within about two hours of termination (e.g. about one hour, about one and a half hours, or about two hours). Administration can be terminated by, for example, removing or deactivating a desmopressin delivery device, or by exhausting the drug so in the delivery device. At termination, delivery may cease completely or may continue at a level insufficient to maintain a supra-threshold concentration of desmopressin in the blood.

The desmopressin can be administered at a relatively constant flux rate sufficient to establish and maintain a concentration in the blood within the desired range. Alternatively, the rate of administration can vary significantly over the course of administration. For example, the desired concentration can be achieved initially by administering a bolus of desmopressin in an amount sufficient to establish the slightly supra threshold concentration in the blood, or by administration of desmopressin at a flux rate that promptly establishes the desired concentration. The desired concentration then can be maintained by administering desmopressin at a lower flux rate maintaining the effective concentration for a period of time, i.e., balancing the rate of clearance by the body so as to keep the concentration more or less constant. As the objective is to establish and maintain an effective concentration in the blood of the patient just above the threshold concentration that activates water channels, the dose and rate of administration can be adjusted based on the size and/or metabolic rate of the patient, for example. In certain embodiments, desmopressin is administered at a flux rate between about 5 and 35 ng/hour (e.g. between about 10 and 20 ng/hour, between about 20 and 35 ng/hour, or between about 5 and 15 ng/hour). Larger patients have a larger extracellular fluid volume into which the desmopressin will distribute and may therefore require a higher flux rate (e.g. about 30 to 35 ng/hour) to achieve a blood concentration slightly above the threshold level.

In some embodiments, the methods include administering desmopressin with a delivery device (e.g. a "patch") applied to the skin of the patient. In these embodiments, the administration can be terminated by, for example, removing the delivery device, deactivating it, or having it automatically cease drug delivery, e.g., after a pre-determined time. In certain embodiments, the delivery device includes a desmopressin flow switch for initiating or terminating a flow of desmopressin to the patient. In particular embodiments, the delivery device includes a solution flow control means and the method includes actuating the control means to initiate a first, higher flux rate to establish the desmopressin concentration in the blood and to initiate a second, lower flux rate to maintain the concentration, thereby maintaining a substantially constant predetermined desmopressin concentration in the blood of the patient.

Thus, in addition to providing methods of modulating urine production, the invention also provides devices useful for establishing and maintaining a desired concentration so of desmopressin in the blood. In one embodiment, the devices include a depot containing a solution of desmopressin in a pharmaceutically acceptable carrier, a skin interface member in fluid communication with the depot for application to the skin of a patient, and a means for delivering the desmopressin solution from the depot to the interface member and intradermally or transdermally to the blood of a patient.

Drug delivery is controlled at a flux rate which is sufficient to establish a desmopressin concentration in the blood of the patient within the range of at least about 0.2 pg/ml and up to as high as about 5 pg/ml, advantageously no greater than 2 pg/ml. The flux rate may be about 5, 10, 15 ng/hr, 20 ng/hr, 25 ng/hr, or between 30 to 35 ng/hr (i.e., 5000, 10,000, 15,000, 20,000, 25.000, or 30.000 to 35,000 pg/hr), advantageously about 10-20 ng/hr, more advantageously about 5-15 ng/hr, and may vary as disclosed herein. Note that a flux rate of about 10 ng/hr can maintain in a 70 kg adult a steady blood concentration of about 1.3 pg/ml, which is at or about (i.e., just above) the threshold desmopressin concentration sufficient to activate water channels. In embodiments of the devices in which desmopressin is in solution, the desmopressin solution disposed in the depot desirably may have a concentration less than 5.0 μg/ml, and preferably in the range of 0.25 to 2.0 μg/ml.

Maintaining a desmopressin flux that results in a desmopressin concentration just above the threshold serves to activate the water channels—and to reduce or terminate normal urine production. Stopping the desmopressin flux, e.g., by removing the device from contact with the skin, results in drug concentration falling rapidly below the threshold at which water channels are activated and re-establishment of normal urine production. The devices described herein thus can activate and inactivate water channels in the kidneys of the patient, thereby suppressing or resuming urine production, within a relatively short response time. Thus, in one embodiment, the device may initially deliver a relatively high flux to achieve rapidly a serum desmopressin concentration in the desired antidiuretic range, and then a lower flux to maintain the desired low dose desmopressin concentration. Terminating the flux, either by removing the device from the skin or by exploiting mechanisms built into the device as disclosed herein, permits normal clearance mechanisms rapidly to reduce desmopressin blood concentration. Because the concentration is just over the activation threshold to begin with, urine production is restored quickly, e.g., in 0.5 hour, 1.0 hour, or perhaps 2.0 hr, depending on the initial desmopressin concentration and on the physiology of the patient.

In embodiments that employ transdermal delivery, the desmopressin solution is formulated for transdermal delivery using techniques known to those in the art for administration of peptides; and the interface member includes a desmopressin solution-permeable surface for contact with the exterior of the skin (epidermis) of the patient. In embodiments that employ intradermal delivery, the interface member may include one or more microstructures. Microstructures, which can include microneedles, perforators, and other small forms suitable for insertion into the skin, such as micropellets, can be used singly or in combination, e.g., in an array, to penetrate the stratum corneum or epidermis of the patient. Desmopressin is delivered to the dermis through or from the microstructure, which provides access to blood and lymph. It is also contemplated that dried or lyophilized desmopressin might be applied to be embedded within a microstructure, such as a microneedle. Upon application of the device when the microneedles come in contact with the patient's blood supply in the intradermal compartment, the formulated desmopressin is dissolved or if in solution released and is absorbed into the blood stream at the desired flux rate, which terminates when the desmopressin depot is exhausted. Design of such devices is facilitated significantly by the very low desmopressin flux rates and blood concentrations required for operability. It is further contemplated that desmopressin may be incorporated into an extrudable solid dosage form that can be injected into the intradermal or subcutaneous compartments in the form of a micropellet by an appropriate syringe-like device allowing rapid or sustained release of the drug.

Thus it will be apparent that many specific embodiments of the delivery devices of the invention may be constructed by adapting known intradermal and transdermal drug delivery technology and engineering principles disclosed in the patent literature and available commercially. The adaptation involves one or a combination of control of desmopressin drug concentration, control of solution viscosity and other flow properties, formulation of desmopressin with additives which enhance/inhibit transdermal flux, controlling permeability rates through membranes (either by selection of membrane material, pore structure, or some combination of both), use of microneedles of appropriate number and interior diameter, use of drug coated or matrix embedded microstructures, use of mechanisms for flow control. etc. so as to achieve the flux rates and thus the blood concentrations and bioavailability profiles disclosed so herein. Furthermore, this known technology may be used to design specific devices for different patient groups. Thus the flux rates and profiles may differ for devices intended for groups of patients having different blood volumes and/or different metabolic rates. For example, an optimal flux rate profile for geriatric patient might be different from middle-aged adults, men different from women, children different from adults, etc. A device adapted for children weighing, for example, between 15 and 35 kg, might be ideal for treatment of PNE, while avoiding a minimizing risk that the patient develops hyponatremia.

A formulated desmopressin solution may be delivered from a depot of desmopressin solution within the device to a skin interface member by means of, e.g., simple passive absorption or adsorption, hydraulic pressure exerting means such as a spring; electrophoretic drive apparatus; or phonophoretic (ultrasonic) apparatus for impelling the solution from the device at a predetermined rate. In one embodiment preferred for its simplicity, the delivery means may include a volume of the solution in contact with a back surface of a skin interface member (distal to the surface which contacts the skin), and the desmopressin flux may be established by absorptive flow of the solution into the interface member together with diffusion from the interface member through the skin of the patient. In another, the solution is transported by capillarity or impelled flow through one or more microneedles extending from the interface member to the intra dermal compartment of the patient's skin.

The device also may include a desmopressin solution flow controller for regulating the flux rate of desmopressin into the blood of the patient. This may take the form of an inherent property of the device, for example, one in which an amount of dried desmopressin exposed to blood at the outset is high, so that the influx rate is high. As the dried drug dissolves and is transported away from the site of application, less dried drug is available for absorption and the flux drops, until negligible drug is being delivered, and the antidiuretic effect ceases. In other embodiments, an active solution flow controller establishes a first, higher flux rate to establish a preselected desmopressin concentration within the blood of a patient and a second lower flux rate to maintain the concentration. Such an active device also may include a timer for triggering the flux rate change, and/or a desmopressin solution flow switch for initiating or terminating the flow of desmopressin into the blood of the patient.

In another embodiment, the interface member of the device comprises a microstructure (e.g. a microneedle or micropellet), or an array of microstructures, which penetrates the stratum corneum of the patient. The microstructure(s) may be coated with an amount of desmopressin sufficient to establish upon engagement with the skin a first, higher flux rate to establish a preselected low desmopressin concentration within the blood of a patient. Optionally, the microstructure (s) are fed by solution from the depot of a concentration and at a flow rate suitable for establishing and maintaining a desmopressin concentration within the desired low dose range. Alternatively, a solution flow controller which establishes a second, lower flux rate at a predetermined time to maintain the concentration thereby to produce a predetermined interval of substantially constant predetermined desmopressin concentration in the blood of the patient.

Other embodiments and details of the invention are presented herein below.

BRIEF DESCRIPTION OF THE DRAWINGS

The invention is herein described, by way of example only, with reference to the accompanying drawings, wherein dimensions are not to scale, but rather are selected as a means of describing the structure and operation of the various devices discussed, and wherein.

Like reference characters in the various drawn figures indicate corresponding parts.

DETAILED DESCRIPTION OF THE INVENTION

Figure 1:
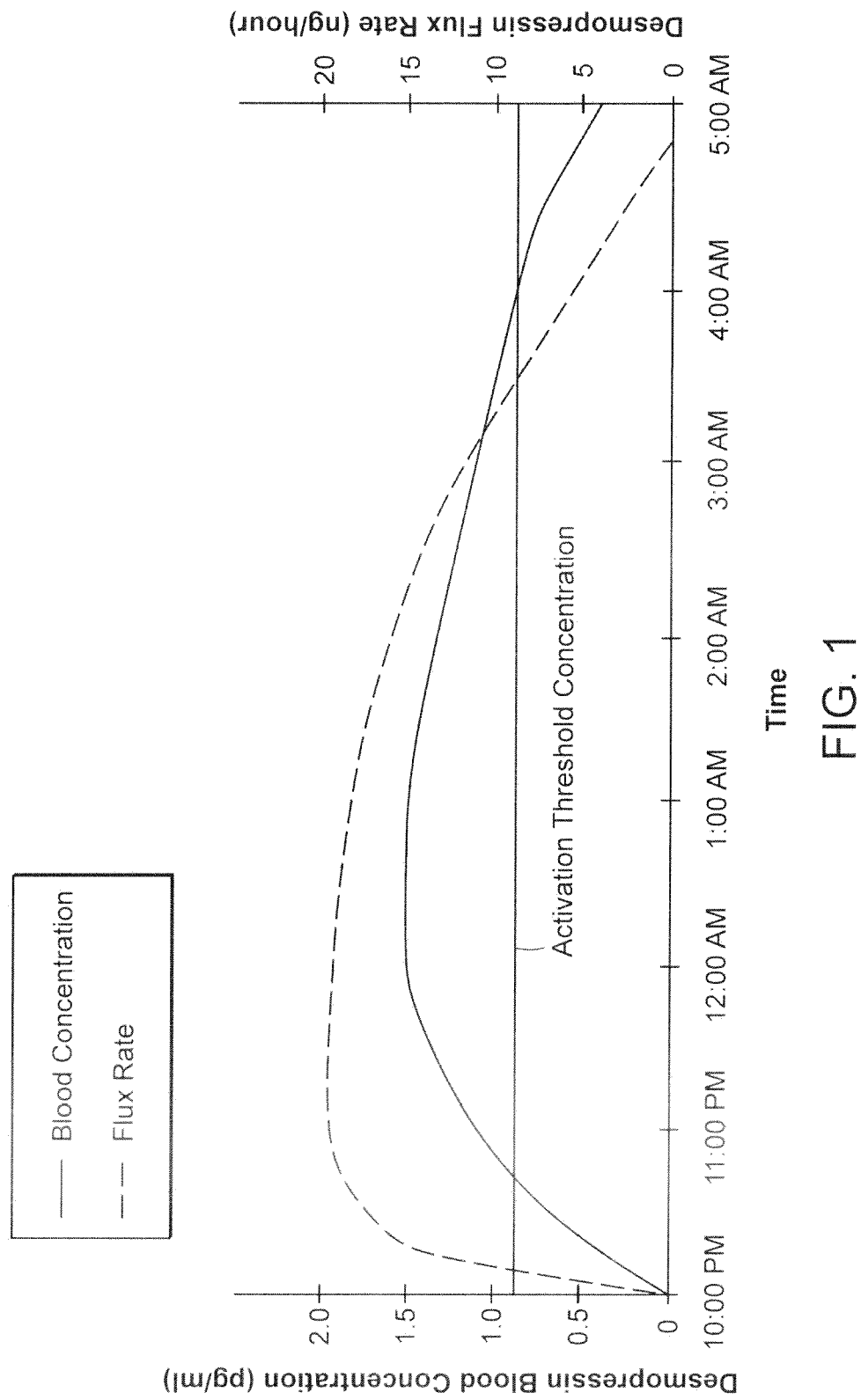
FIG. 1 is a graph of desmopressin blood concentration and variable flux rate vs. time illustrating a 7-hour operation of a device and method embodying the invention.

For convenience, certain terms used in the specification and examples are set forth below.

"Treating", includes any effect, e.g., lessening, reducing, modulating, or eliminating, that results in the improvement or modulation of the condition, disease, disorder, etc.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all physiologically acceptable solvents, dispersion media, coatings, antibacterial and antifungal agents, isotonic and absorption delaying agents, preservatives, and the like.

The invention provides new solutions to the problem of treating patients for conditions characterized by overproduction of urine, inadequate urine concentration, low urine osmolality, or excessive frequency of urination, e.g., central diabetes insipidus, primary nocturnal enuresis, nocturia, urinary urgency and frequency during waking hours, incontinence, or unwanted production of urine resulting in urine leakage at rest or by exertion or stress.

Desmopressin has a known anti-diuretic pharmacological effect which results in production of smaller volumes of more concentrated urine. For patients with central diabetes insipidus, the pituitary gland produces little or no vasopressin, the natural anti-diuretic hormone. This deficiency results in large volumes of very dilute urine being produced which can lead to dehydration and serious metabolic abnormalities unless the patient consumes very large volumes of water. Desmopressin administered multiple times each day replaces the deficient vasopressin and restores urine concentration and volume in these patients to levels nearer the norm. In a manner similar to insulin administration to patients with diabetes mellitus, desmopressin is titrated by the patient seeking a balance of fluid intake and urine output.

In patients with primary nocturnal enuresis (bed wetting), the anti-diuretic effect of desmopressin decreases urine volume at night, lowering the amount of urine which the urinary bladder must retain and, thereby decreasing or eliminating occurrences of enuresis.

In patients with adult nocturia, there is either polyuria (production of large amounts of urine) at night, low bladder capacity, incomplete bladder emptying, or increased bladder sensitivity to urine volume. Under any of these circumstances, the bladder's threshold for urine retention is exceeded during the night, resulting in neurological signals for voiding. This awakens the patient in order to void, interrupting sleep. Desmopressin's known anti-diuretic effect decreases urine production at night, delaying the time when the voiding threshold is exceeded, resulting in a longer sleep period before voiding, and decreasing the number of nocturnal voids.

In patients with urinary urgency and frequency during waking hours often related to overactive bladder (OAB), the bladder is overly sensitive to relatively small volumes of urine resulting in the need for frequent voiding of small amounts of urine. Desmopressin's known anti-diuretic effect can decrease urine production resulting in voiding postponement for several hours during time periods when it is inconvenient for the patient to void.

In patients with incontinence of various types (stress, urge, etc.) often related to urinary bladder abnormalities from surgery, childbirth, or aging, the bladder is unable to retain even normal volumes of urine. The volume threshold for voiding is low and there is a high risk of involuntary voiding (incontinence). This can be brought on by physical activity or stress. Many patients, particularly women, wear urine absorptive pads to avoid the embarrassment and inconvenience of unwanted urine leakage. Desmopressin's known anti-diuretic effect decreases urine production, allowing for voiding postponement because there is a delay in crossing the abnormally low volume threshold for voiding in these patients.

Two problems stand in the way of the use of desmopressin routinely and relatively casually by adults (or children under the supervision of adults) to postpone voiding or to temporarily inhibit urine production. The first is desmopressin's exceedingly low and variable bioavailability when administered orally or intranasally. This inhibits, for example, self administration of a low but effective dose of the drug, for example, after urination but before playing tennis, or chronically before bed to prevent nocturia or enuresis. The "solution" to this heretofore has been to provide dosage forms of low bioavailability, but with far more active than is needed to achieve an anti-diuretic effect.

This solution is, however, unsatisfactory, because of the second problem: retention of too much water in the body causing low blood osmolarity. The high doses of desmopressin variably produce blood concentrations far in excess of the anti-diuretic threshold, resulting in prolonged anti-diuretic effect typically of unknown duration and water retention. If the patient drinks, he may be unable to maintain salt balance within acceptable range because his water channels are activated, and blood volume remains high. This state, known as "water intoxication," produces hyponatremia, a dangerous side effect of desmopressin therapy in which serum sodium falls to abnormally low levels. Hyponatremia can result in seizures, cardiac arrhythmias, cerebral edema and death. When desmopressin is administered non-invasively, e.g., orally or transmucosally, the low and variable bioavailability from patient to patient and dose to dose result in a wide and unpredictable range of blood levels which are much more difficult to control, and which make hyponatremia more likely to occur.

The family of devices disclosed herein precisely deliver a desmopressin flux through the skin of a patient to induce—preferably rapidly—a blood concentration within a relatively narrow, low range at just the level necessary to achieve the desired anti-diuretic effect, thereby permitting normal drug clearance mechanisms to lower the blood concentration quickly below the anti-diuretic threshold, and to minimize undesirable side effects such as hyponatremia. The low dose sustained delivery devices thus permit the desmopressin flux to be shut off so that blood concentration of desmopressin drops relatively quickly below the water channel activation threshold, permitting return to a state of normal urine production.

The devices and methods disclosed herein bring distinct and important health and social benefits to patients and their caregivers. Until now the amount of desmopressin prescribed for treatment of central diabetes insipidus, enuresis, nocturia, frequency, daytime voiding postponement or incontinence has actually been far more than necessary to achieve just the desired effect, which is to act as an anti-diuretic, inhibit urine production, and prevent dehydration. The inventors have found that too high a desmopressin blood concentration results in an extended anti-diuretic effect that lingers as the desmopressin is cleared from the blood, such that return to normal urine production (and the patient's normal routine) is unnecessarily prolonged, and can lead to increased risk of developing hyponatremia. Provision of a device that administers transdermally or intradermally a sustained low dose (low $C_{max}$) of the drug just above the activity threshold permits return to homeostasis rapidly, and enables the patient to control his or her urine production intelligently, safely, and conveniently.

When treating urinary conditions such as incontinence, enuresis, nocturia, frequency or central diabetes insipidus, the psychological well-being of the patient is perhaps as important as his or her physical comfort. These conditions are disruptive of sleep patterns (enuresis, nocturia) and of normal, daily activity (incontinence). The ability of patients suffering from these conditions, who are candidates for treatment with desmopressin to alleviate their urine overproduction, to carry on or return to normal, predictable routines taken for granted by the population at large, is an important aspect of their treatment.

The devices and methods disclosed herein thus permit reliable, non-invasive low dose and convenient treatment for patients suffering from conditions characterized by overproduction of urine or inability to control voiding at some level. The devices are worn on or adhered to the skin, and deliver a consistent, low, reproducible flow of desmopressin or analogs thereof to the patient at precisely the level needed to suppress urine overproduction, and quickly shut off delivery of the drug when programmed or removed (as influx terminates), at which time normal urine production returns, e.g., when the patient awakes from sleep, or at an interval that the patient or caregiver determines, e.g., at the end of a long trip when it is convenient or possible for the patient to urinate in an appropriate location. Fluid intake is restricted during the time the anti-diuretic effect endures.

In one embodiment, devices for modulating urine production in a patient include a depot containing a solution of desmopressin in a pharmaceutically acceptable carrier. An interface member for application to the skin of a patient, such as a permeable pad for attachment to the skin, or one or an array of microneedles, are in fluid communication with the depot. The devices comprise various means for delivering the desmopressin solution from the depot to the interface member and downstream intradermally or transdermally to the blood of a patient. The flux rate of the desmopressin is controlled by setting the concentration of desmopressin in the depot, in combination with controlling either the rate of flow of solution from the depot, the rate of flow of solution to the interface member, the rate of flow of solution from the interface member into the body of the patient, or by exploitation of some combination of these control points. In any event, the influx rate is controlled to be sufficient to establish a desmopressin concentration in the blood of the patient just above the water channel activation threshold, e.g. within the range of 0.1 to about 2.5 pg/ml, advantageously no greater than 1, 1.5, 2, or 2.5 pg/ml. The flux rate in any case is insufficient to induce a desmopressin concentration in the blood of the patient to a level greater than about 15 or 20 pg/ml. The flux rate may be between about 5, 10, 15, 20, 25, or 30 to 35 ng/hr (i.e., 5000, 10,000, 15,000, 20,000, 25,000, or 30.000 to 35.000 pg/hr), advantageously about 10-20 ng/hr or 20-35 ng/hr, more advantageously about 5-15 ng/hr, so as to establish the desired blood concentration for a reasonable, predetermined time before the patient or the device shuts off desmopressin flow. The skilled artisan will readily be able to develop a device for pediatric use in view of the disclosure herein.

This flux rate preferably is set so that, given the desired blood concentration and the known clearance rate of desmopressin (half life of about 1.5 to 2.0 hours), the patient reaches the desired low but supra-threshold blood concentration in a reasonable time, e.g., less than an hour (and generally, the sooner, the better), and is maintained within a low dose range just above the activation threshold (approximately within the range of 0.5 to 1.5 pg/ml) for a desired time period (e.g., two hours for a workout, or 4-6 hours or 5-8 hours for treatment of nocturia). Termination of the flux by automatic or manually actuated mechanisms built into the device, or by removal of the device from contact with the skin, results in normal drug clearance mechanisms of the body of the patient rapidly reducing the low concentration to a still lower concentration, below the activation threshold.

Desmopressin and any of its salts or analogs may be used in the invention. The desmopressin may be in the form of the free base or a pharmaceutically acceptable salt, or in any other pharmaceutically acceptable form. The acetate salt is particularly useful. Suitable desmopressin analogs include arginine vasopressin, lysine vasopressin and small molecule V2 agonists. Use of the term "desmopressin" herein should be construed to embrace these and other analog forms of desmopressin or vasopressin. The desmopressin solution is desirably formulated for efficient transdermal or, preferably, intradermal delivery. Such formulations and formulation methods for adaptation to the administration of various peptides are within the skill of those of so ordinary skill in the art, and need not be set forth here except as specifically exemplified herein. The formulation may include a preservative to extend the shelf life of the device. Various options for formulation of transdermal dosage forms are disclosed in the art. Dosage forms designed for intradermal administration also are well known, and can be the same as or similar to intravenous dosage forms, or comprise carbohydrate based films or matrices incorporated into, coating the surface of, or filling cavities within microstructures.

The interface member of the device may comprise a desmopressin solution-permeable membrane defining a surface for contact with the skin of the patient. The desmopressin solution-permeable surface permits delivery of the desmopressin from the depot through or to the skin of the patient. For highest bioavailability and precision of delivery, intradermal delivery is preferred. Intradermal delivery permits direct delivery to a vascularized compartment resulting in rapid absorption into the systemic circulation and correspondingly rapid on/off effects. While transdermal delivery is contemplated, its use is more subject to variable bioavailability due to the stratum corneum functioning as a physical barrier to drug reaching the epidermis, and to the creation of a depot of drug in the epidermis.

Accordingly, transdermal delivery methods and devices can benefit from techniques that reduce the efficacy of the stratum corneum as a barrier to drug entry. These include, for example, mechanical methods for removing portions of the stratum corneum before applying a transdermal desmopressin delivery device. "Tape-stripping," in which tape is pulled from the skin of the patient, removes skin cells and can increase skin permeability, but is painful and relatively uncontrolled. A more desirable method for removing the stratum corneum has been described in U.S. Pat. No. 5,441,490 (the complete disclosure of which is hereby incorporated by reference), in which suction is used to form a blister. Removal of the blister permits subsequent transdermal delivery of desmopressin without the interference of the stratum corneum, as described in Svedman et al. (1991) *The Lancet* 337:1506-1509, the complete disclosure of which is hereby incorporated by reference. The skin can also be "micropunctured" to introduce "micropassages" or "microfissures" across the stratum corneum, to enhance subsequent transdermal delivery. Such devices and methods are described, for example, in U.S. Pat. Nos. 5,611,806; 5,843,114; and 5,879,326, and in Wermeling et al. (2008) "Microneedles permit transdermal delivery of a skin-impermeant medication to humans," *PNAS* 105 (6):2058-2063, the complete disclosures of each of which are herein incorporated by reference. Once the so stratum corneum has been punctured, stripped, or removed by suction, a transdermal delivery device of the invention can be applied to deliver low dose desmopressin with favorable pharmacokinetics.

The permeability of the stratum corneum can also be enhanced by treatment with a chemical permeability enhancer, such as dimethylsulfoxide, decylmethylsulfoxide, diethylene glycol monomethyl ether, diethyleneglycol monoethyl ether, sodium laurate, sodium lauryl sulfate, cetyltrimethylammonium bromide, benzalkonium chloride, lecithin (see, for example, U.S. Pat. No. 4,783,450, the teachings of which are hereby incorporated by reference), 1-n-dodecylazacycloheptan-2-one (see, for example, U.S. Pat. Nos. 3,989,816; 4,316,893; 4,405,616; and 4,557,934, the teachings of which are hereby incorporated by reference), ethanol, propanol, octanol, benzyl alcohol, lauric acid, oleic acid, valeric acid, isopropyl myristate, isopropyl palmitate, methylpropionate, ethyl oleate, propylene glycol, ethylene glycol, glycerol, butanediol, polyethylene glycol, polyethylene glycol monolaurate, urea, hydroxide (see, for example, U.S. Pat. No. 6,558,695, the teachings of which are hereby incorporated by reference), dimethylacetamide, dimethylformamide, 2-pyrrolidone, 1-methyl-2-pyrrolidone, ethanolamine, diethanolamine, triethanolamine, salicylic acid, citric acid, succinic acid, and permeability enhancing peptides (see, for example, U.S. Pat. No. 5,534,496, the teachings of which are hereby incorporated by reference).

Energy can also be used to ablate or otherwise increase the permeability of the stratum corneum. For example, electrodes can be used to generate micro-channels in the stratum corneum. A suitable device is described in U.S. Pat. No. 6,148,232, and its use to pre-treat skin prior to transdermal peptide administration (as a dried or lyophilized component of a printed "patch") is described in U.S. Pat. No. 7,383,084, the disclosures of each of which are hereby incorporated by reference. While lasers are also useful in ablating the stratum corneum to improve permeability, the public's limited access to medical lasers generally renders them less convenient than other skin permeabilization techniques.

In addition to passive transdermal delivery systems, active systems can be used to drive low doses of desmopressin transdermally. One example of an active transdermal delivery system based on electrolytic delivery of polypeptides is disclosed in U.S. Pat. No. 4,878,892, the teachings of which are hereby incorporated by reference. This system is capable of delivering biologically effective amounts of a polypeptide without significant cutaneous toxicity (see U.S. Pat. No. 4,878,892 and Meyer et al. (1988) "Successful transdermal administration of therapeutic doses of a polypeptide to normal human volunteers," *Clin. Pharmacol. & Therapeutics* 44(6):607-612).

An efficient means of desmopressin delivery from the depot to the skin is intradermal administration, via an interface member comprising one or more microneedles which penetrate the stratum corneum of the patient and enable fluid communication between the depot and the epidermis or direct contact with surfaces or cavities in the microneedles coated with or containing desmopressin. The length and size of the microneedles are adequate to penetrate the stratum corneum but small enough to produce little if any sensation for the patient. For example, suitable lengths are about 0.3 to 1.5 mm, advantageously between about 0.8 to 1.1 mm. An example of a single needle device is provided in U.S. Pat. No. 6,939,324, the teachings of which are herein incorporated by reference.

A plurality of microneedles, e.g. in an array, may be desirable if more surface area for delivery, or a more flexible patch, is desired. The microneedles may each have a channel that transports fluid from the depot to the needle end, or the microneedles may otherwise allow for fluid delivery from the depot, e.g., with perforated or porous walls. Alternatively, the microneedles may be coated with a desmopressin preparation or contain a film or matrix of desmopressin in cavities or in the material structure of the microneedle itself, to provide a burst of desmopressin upon application so as to aid rapid achievement of the threshold activating concentration, optionally with desmopressin solution passing through the needles to help achieve, or to maintain the desired concentration.

A benefit to microneedle devices is that the microneedles also may serve to help keep the channel created thereby open for subsequent drug delivery or body fluid monitoring. In an embodiment, microneedles may be made from a solid matrix of dissolvable (including meltable) or biodegradable material that optionally holds a predetermined amount of desmopressin. The matrix can be composed of fast-dissolving and/or swelling materials. A variation of dissolvable or biodegradable microneedles is the "micropellet" which is injected into the intradermal or subcutaneous compartments and can be composed of fast-dissolving and/or swelling materials. A micropellet or other injectable microstructure can be administered using an injection system such as those described in U.S. Patent Application Publication Nos. 2003/0054044 and 2006/0161111, the complete disclosures of which are incorporated by reference herein.

Suitable matrix materials used to make the microneedles include, for example, ceramics; metals, such as stainless steel or titanium; and polymers, such as poly(methylmethacrylate), polyethylene, polypropylene, polyvinylpyrrolidone (PVP), polyethylene glycol (PEG), polyvinyl alcohol (PVA), cellulose, hydroxypropyl cellulose (HPC), hydroxyethyl cellulose (HEC), hydroxypropyl methylcellulose (HPMC), dextrin, mono- and polysaccharide, sodium carboxymethyl cellulose, polyalcohol, gelatin, gum arabic, alginate, chitosan, cyclodextrin and other biopolymers. Useful biodegradable polymers include, for example, poly-lactic acid (PLA), polyglycolic acid (PGA), and their copolymers (PLGA). Carbohydrate derivatives, such as sugar derivatives (trehalose, glucose, maltose, lactose, maltulose, iso-maltulose, lactulose, fructose, turanose, melitose, melezitose, dextran, maltotol, sorbitol, xylitol, palatinit and mannitol) may be used. Water-soluble ingredients, such as phosphate, nitrate and carboxylate glasses, magnesium chloride, potassium chloride and calcium chloride can be also used for a matrix material, alone or mixed with a matrix polymer.

Lipophilic additives may include alcohols, polyoxyethylene alkyl ethers, fatty acids, bile acids, glycerol fatty acid esters, acetylated glycerol fatty acid esters, lower alcohol fatty acids esters, polyethylene glycol fatty acids esters; polyethylene glycol glycerol fatty acid esters, polypropylene glycol fatty acid esters, polyoxyethylene glycerides, lactic acid derivatives of mono/diglycerides, propylene glycol diglycerides, sorbitan fatty acid esters, polyoxyethylene sorbitan fatty acid esters, polyoxyethylene-polyoxypropylene block copolymers, transesterified vegetable oils, sterols, sterol derivatives, sugar esters, sugar ethers, sucroglycerides, polyoxyethylene vegetable oils, polyoxyethylene hydrogenated vegetable oils, reaction mixtures of polyols and at least one member of the group consisting of fatty acids, glycerides, vegetable oils, hydrogenated vegetable oils, and sterols, and mixtures thereof.

In microneedle intradermal drug delivery devices of the invention, desmopressin delivery can be controlled by varying design factors including: dimensions of the microneedles, dissolution rate of the matrix, number of microneedles, size and composition of the drug reservoir, and frequency of device usage. For example, devices designed to deliver drug at high rates might have a more active drug-loaded device and/or a faster dissolving matrix. For sustained drug release, fewer microneedles and/or use of a slow(er) dissolving or semi-solid matrix may be useful. Combinations of such microneedles may be used to achieve high early flux rate followed by sustained lower flux rate.

The use of dissolvable microneedles is also contemplated, as their use avoids, in some cases, pain and/or irritation caused by metal needles or piercing elements. U.S. Pat. No. 7,182,747, for example, discloses "solid solution perforators" which may be adapted for use in the inventions disclosed herein. In contrast to conventional hollow needle technologies, these microneedles are made from a solid matrix of dissolvable or biodegradable material that optionally holds one or more selected drugs and is formed into one or more perforators. The matrix can be composed of fast-dissolving and/or swelling materials. The solid solution can be a homogeneous or non-homogeneous phase or porous solid solution, for example, a solid made from an emulsion or suspension. Particles for a microneedle can be molded into a desired form as described, for example, in U.S. Patent Application Publication No. 2002/0082543 and International (PCT) Publication No. WO 2007/127976, the teachings of each of which are hereby incorporated by reference. Microneedles molded from a biodegradable, protein-impregnated PLGA polymer can pierce skin and release the protein at a controlled rate over a period of hours, as described in Park et al. (2006) "Polymer Microneedles for Controlled-Release Drug Delivery," *Pharm. Res.* 23(5):1008-1019, the teachings of which are hereby incorporated by reference.

Desmopressin solution may be delivered from the device by any precision means known by those of ordinary skill in the art, e.g., hydraulic pressure exerting means, electrophoretic means, or phonophoretic (ultrasonic) means for impelling the solution at a predetermined rate from the depot to the interface member. One exemplary delivery means is disclosed in detail in U.S. Pat. No. 5,848,991, the disclosure of which is incorporated herein by reference.

Such delivery means may be programmable, or may be adjustable to a desired flux rate, or may be switched on or off as needed manually or automatically (e.g., sufficiently prior to or upon the patient's awakening to permit normal urine production to be reestablished). The device thus may include a desmopressin solution flow controller for regulating the flux rate of desmopressin into the blood of the patient. The flow controller may establish a first, higher flux rate to establish a preselected desmopressin concentration within the blood of a patient and a second, lower, flux rate to maintain that concentration. The device may desirably also include a timer for triggering the flux rate change, e.g., so no user intervention is needed; and/or a desmopressin solution flow switch, for initiating or terminating the flow of desmopressin into the blood of the patient; the latter feature will be useful for enabling more patient control, so the patient may determine when he wishes to commence normal urine production. Examples of programmable transdermal or intradermal delivery devices are described in U.S. Pat. No. 6,723,077 and International (PCT) Publication No. WO 2006/060106, the teachings of each of which are hereby incorporated by reference.

Alternatively, the means for delivering may include a volume of the solution in contact with a surface of the interface member distal to the surface for contact with the skin of the patient, and the desmopressin flux is established by absorptive flow of the solution into the interface member and diffusion from the interface member through the skin of the patient.

The device is advantageously small, e.g., on the order of 0.5×1×1 cm, or smaller, so the patient is not disturbed during sleeping by a perceptible "lump" on their skin; or during the day when it might be inadvertently brushed or knocked off. The device may be fixed to the skin by frictional forces, e.g., the engagement of the microneedles on the skin; by an elastic arm band or the like, or using adhesive, such as a ring of adhesive on the periphery of the bottom surface of the interface member.

The devices described herein are used in modulating urine production in a patient in need thereof. The patient will be one for whom the treatment will be beneficial, e.g., one suffering from diabetes insipidus, enuresis, e.g., primary nocturnal enuresis (PNE), nocturia, or incontinence. The device is applied to the skin of the patient and affixed to the skin, whereupon a flux of desmopressin may be initiated sufficient to establish a desmopressin concentration in the blood within the range noted above, and to induce an anti-diuretic condition in the patient for a preselected time until the flux is terminated. Flow may be initiated simply by affixing the device to the skin of the patient, and/or the terminating step may be effected by removal of the device from the skin of the patient. The device may also include a desmopressin solution flow switch for initiating or terminating the desmopressin flow; a solution flow controller which so establishes a first, higher flux rate to establish a preselected desmopressin concentration within the blood of a patient and a second lower flux rate to maintain the concentration thereby to produce a predetermined interval of substantially constant predetermined desmopressin concentration in the blood of the patient.

In some cases, a simplified device omitting the solution flow controller may be appropriate, e.g., as a lower-cost alternative. Disposable, one use devices are a preferred form. For example, the interface member of the device may comprise a micro-needle, or an array of micro-needles, coated with an amount of desmopressin sufficient to establish upon engagement with the skin a flux rate which levels off and then decreases over a preselected time interval. For example, single microneedles or microneedle arrays can be dip-coated in a reservoir containing a biodegradable polymer such as PLGA, as in International (PCT) Publication No. WO 2006/138719, the teachings of which are hereby incorporated by reference. The amount of desmopressin coated on the microneedles may be determined empirically, e.g., as based upon body mass. A maintenance flux rate of about 5 to 15 ng/hr normally is appropriate.

A particularly advantageous embodiment is a patch that the user applies before sleep, or before some other interval of activity where the patient desires to interrupt urine production. The patch may but need not necessarily include an active solution flow control mechanism, e.g., with a user-selectable timing function, so the user can choose the length of time she or he wishes to have normal urine production suppressed, i.e., in the case of sleep, roughly equivalent to or shorter than the desired sleep time. The patient removes the patch from its packaging, sets the delivery time if necessary, and applies the patch to an area of the skin. Desmopressin delivery at the levels and rates described herein then begins, and urine production is suppressed for the desired time. When the flow controller is shut off, the patch is removed, or the desmopressin depot is exhausted, normal urine production returns quickly. In a preferred simple version of the device, the amount of desmopressin in the depot and its engineered flux rate through exhaustion of the depot fixes the delivery time, e.g. five to seven hours, with termination of flux corresponding simply to exhaustion of the patch delivery. Thus, the patient can sleep without having to wake perhaps repeatedly during the sleep hours, or engage in other activity without concern about involuntary voiding.

Turning to the drawings, the operation of devices of the invention will now be so described.

FIG. 1 illustrates operation of an exemplary embodiment of the invention in treating a patient for whom shutting off urine production is desired, e.g., treating nocturia. A device according to the invention that delivers a low dosage/low variable flux of desmopressin to a patient is affixed to the skin of a patient, the patient urinates, and the device is activated at 10:00 P.M. FIG. 1 shows illustrative and exemplary blood desmopressin concentrations and the flux rates for this patient at various times following application or activation of the device. At one hour (11:00 P.M.), the desmopressin flux rate has peaked at about 20 ng/hr and has raised the patient's blood desmopressin concentration to over about 1.0 pg/ml, i.e., above the concentration sufficient to activate kidney water channels and to induce an antidiuretic effect (here illustrated as being at a blood concentration of about 0.8 pg/ml). At 2 hours (midnight), the flux rate is decreasing slightly but is still in the 20 ng/hr range, and blood desmopressin concentration is elevated to about 1.5 pg/ml. These values decrease slowly but are relatively constant for the next 2.5 to 3 hours. After about 5 hours (3:00 AM), the flux rate has decreased to a level where the activation concentration of desmopressin cannot be sustained. As the flux rate continues to drop, the blood desmopressin concentration falls below the water channel activation level, and urine production commences (here at about 3:45 AM). By 5:00 AM blood concentration is below about 0.5 pg/ml and flux rate has dropped to zero. By 6:00 AM the patient is awake and feels a normal urge to void as urine has been produced for the last hour and a half or so of her sleep. During the sleep there is a sustained antidiuretic interval, little or no urine production, and no bothersome or sleep-interrupting urge to void.

Figure 2:
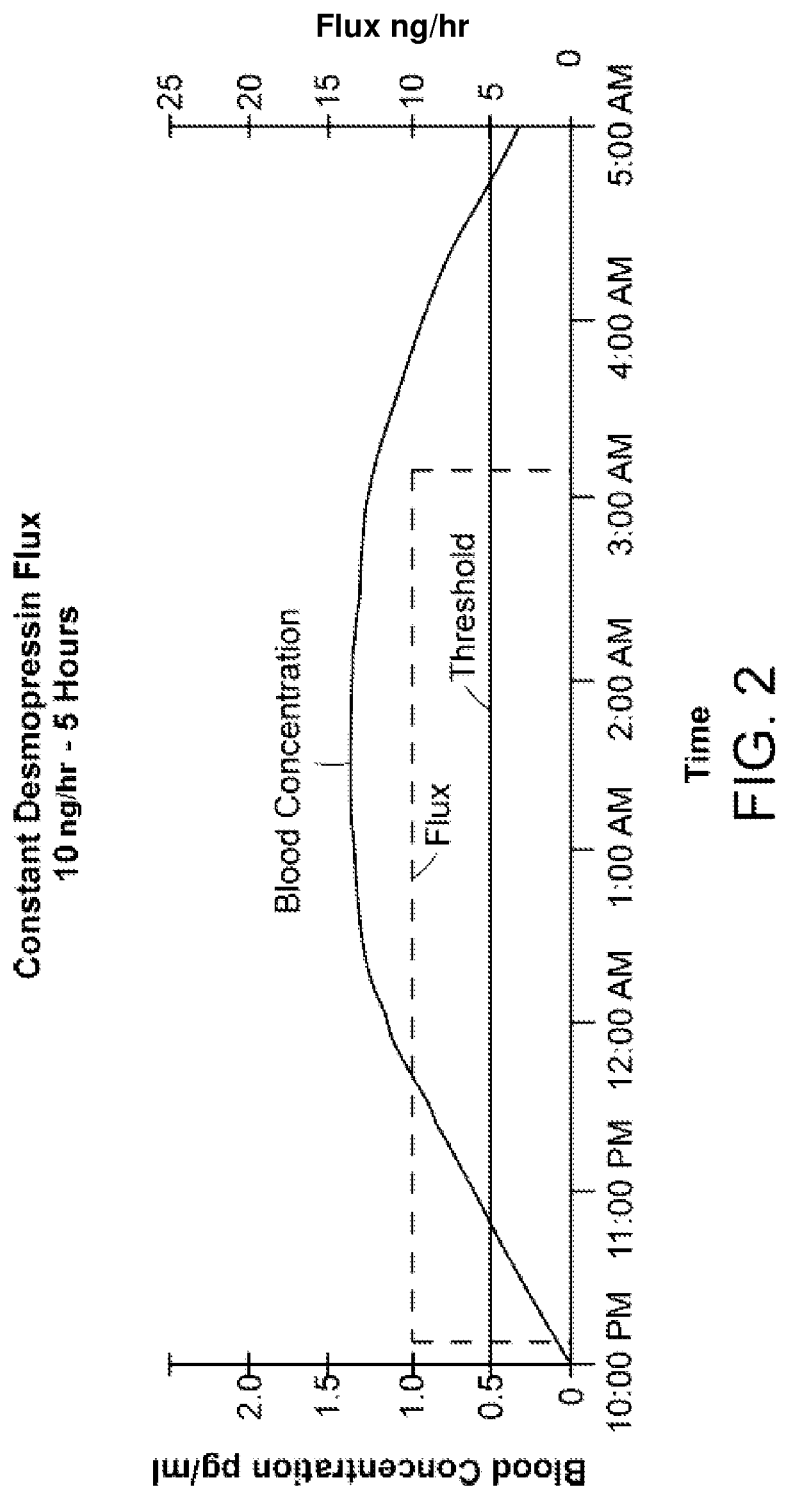
FIG. 2 is a graph of desmopressin blood concentration and constant flux rate vs. time illustrating a 7-hour operation of a device and method embodying the invention.

FIG. 2 illustrates another exemplary embodiment of the invention for treating a patient to shut off urine production, e.g., treating nocturia. A device according to the invention that delivers a low dosage constant flux of desmopressin is affixed to the skin of the patient. The device is activated (if necessary) and the patient urinates at 10:00 PM. FIG. 2 shows illustrative and exemplary blood desmopressin concentrations resulting from a flux of 10 ng/hr over a five hour infusion from 10:00 PM to 3:00 AM relative to the threshold blood concentration for desmopressin's antidiuretic effect. Within about an hour from flux initiation the blood desmopressin concentration exceeds the threshold level and begins to exert an antidiuretic effect. The blood concentration approaches a more or less stable range within about two to three hours so (between about 1.0 and 1.5 pg/ml) which is sustained during the remainder of the five hour flux until 3:00 AM. At this time the flux is discontinued (e.g. timed out or exhausted). Now the blood desmopressin concentration decreases from clearance mechanisms in accordance with the drug's elimination half life, falling below the threshold approximately two hours later (5:00 AM). By 7:00 AM the patient has produced urine, and wakes to void.

The foregoing examples are for illustrative purposes only. The activation concentration will of course vary among individuals, as will blood volume. The important principle in the operation of the device is that the antidiuretic effect can be controlled safely, as the diuretic action is maintained by maintaining a low desmopressin concentration by a continuous low influx of the drug, and an interruption of the influx permits the body to rapidly clear the drug and to re-establish normal urine production. This means that the patch devices of the invention are characterized by improved safety as compared with known desmopressin dosage forms, with little or no risk of development of water intoxication when used as directed.

FIGS. 3-6 schematically illustrate embodiments of low-dose desmopressin delivery devices of the invention.

Figure 3:
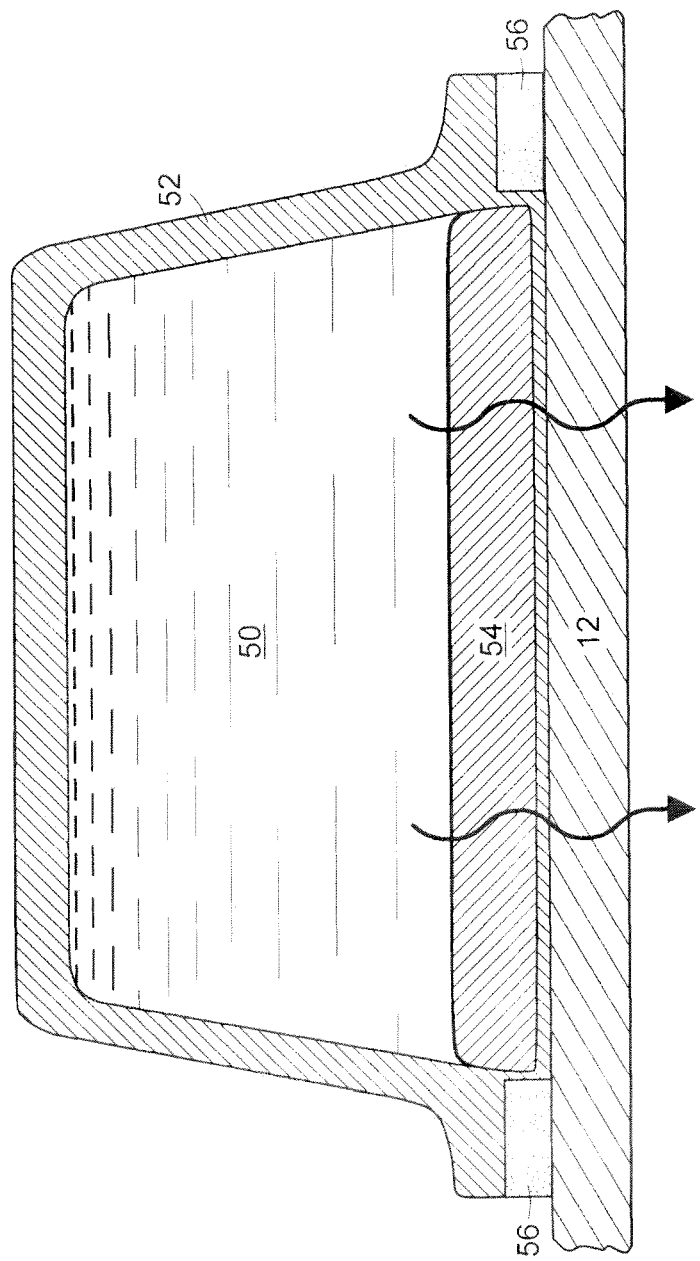
FIG. 3 is a schematic cross-sectional view of a first form of desmopressin delivery device exploiting transdermal delivery.

FIG. 3 depicts a passive embodiment of the invention designed for transdermal operation. It comprises a desmopressin solution disposed within depot 50 defined by a housing 52 comprising wall and top portions and a permeable membrane interface member 54. Importantly, although depot 50 is depicted in FIG. 3 as a single reservoir, it may include a number of reservoirs. For example, depot 50 can include a structured layer (not shown) formed of polygons or other structures serving as a multiplicity of reservoirs, as described in U.S. Pat. No. 6,893,655, the teachings of which are hereby incorporated by reference. The device is adhered to the skin 12 of a patient via a peripheral ring of adhesive 56. The flux rate of desmopressin is controlled by controlling the formulation and concentration of active in the desmopressin solution and by fixing the permeability of the permeable membrane interface member 54. The duration of the antidiuretic interval it achieves is fixed by the flux rate together with the mass of solution disposed in the depot. This embodiment does not exploit active pumping or mechanical pressure to impel the drug through the interface member 54 but rather operates via diffusive effects. In operation, once a protective release cover strip (not shown) is peeled away and the device is adhered to a selected area of the skin of the patient, the drug in the depot 50 is delivered by absorption into and through the permeable membrane 54 (e.g., a so microporous or semi-permeable membrane) and passes through the skin by diffusion. Solution containing desmopressin is removed at the interface of membrane 54 and skin 12 as active is delivered to the circulation transdermally by diffusion, and is replaced by absorption of more solution from the depot or reservoir. This continues until the solution in the depot is exhausted or no longer flows into the membrane. The desmopressin flux rate of this embodiment once established remains essentially constant until exhaustion.

Figure 4:
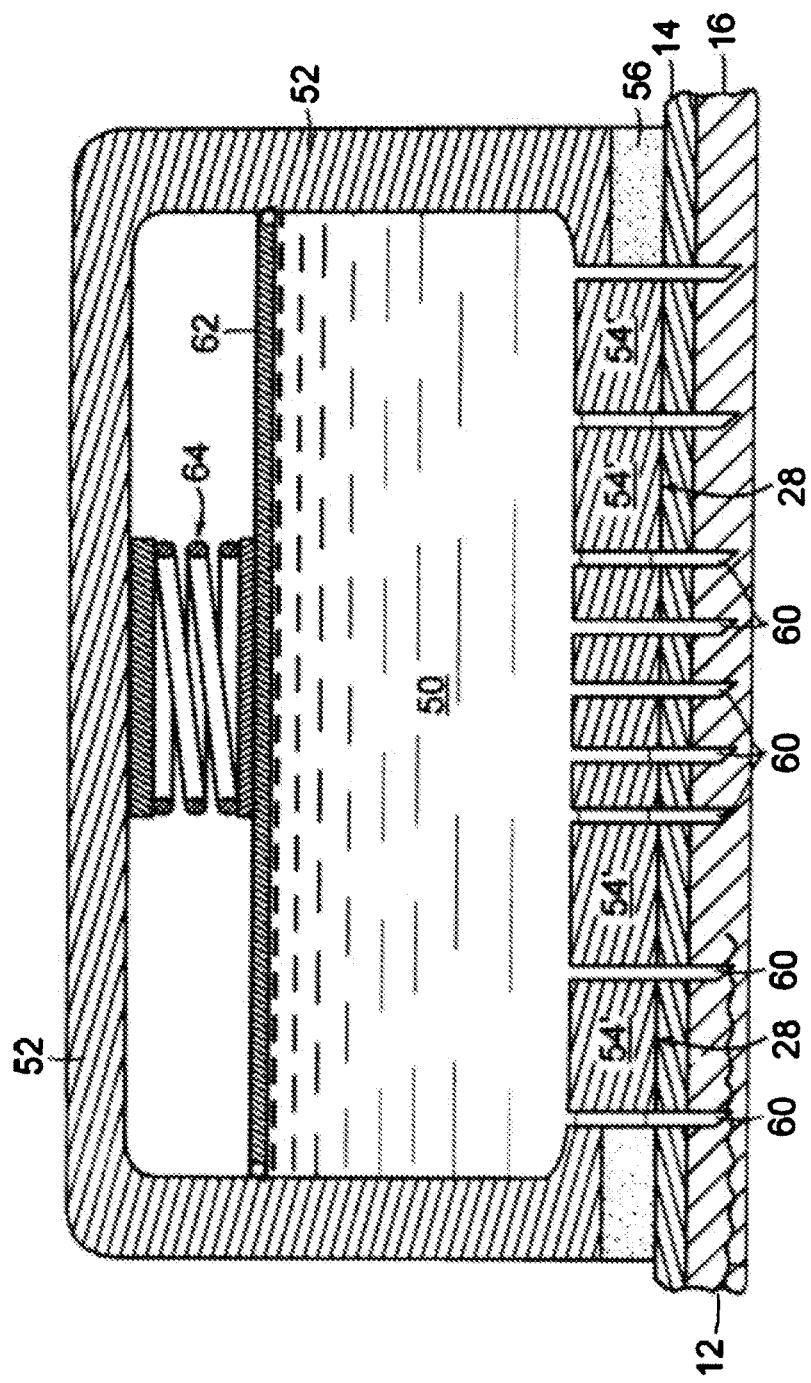
FIG. 4 is a schematic cross-sectional view of a second form of desmopressin delivery device exploiting intradermal delivery.

FIG. 4 schematically illustrates a structure of a device which delivers the drug intradermally, and with a variable flux rate. It comprises a plurality of hollow microneedles 60 fixed within interface member 54' and in fluid communication with drug depot 50. The ends of the needles project outwardly of the bottom surface 28 of interface member 54' a short distance, sufficient to penetrate the stratum corneum 14 and to invade the capillary rich dermis 16 of the subject's skin 12 when the device is applied and adhered to the skin surface. The length and size of the microneedles are adequate to penetrate the stratum corneum but small enough to produce limited discomfort for the patient. Microneedles 60 may project outwardly of the flat surface 28 a distance of 0.3-1.0 mm, just sufficient to penetrate through the epidermis of the subject's skin. The outer diameter of each needle may be (by way of example) from 0.1-0.2 mm and its inner diameter from 0.05-0.075 mm. These dimensions permit a slow, precisely-controlled delivery of the drug from the drug depot 50. The inner end of the hollow needle 27 may be covered by a filter membrane (not shown) to inhibit clogging.

Pressure is applied to the depot 50 via an axially moveable piston 62 mounted for downward movement, fitted with seals, and powered by a spring 64 so as to apply pressure to the depot and to decrease its volume as solution is expelled out through the microneedles to establish a flux into the circulatory system of the patient. Spring 64 here is used illustratively as a means for applying variable pressure to obtain variable flux rates. A combination of springs, a dashpot, or other micromechanical elements may be adapted to control and fix force dynamics. The flux rate is controlled by a combination of factors including the force behavior of the spring or other force exerting mechanical element, the flow properties of the solution in the depot, the concentration of desmopressin in the solution, and the interior diameter, flow through properties, and number of microneedles. The duration of the antidiuretic interval is controlled by the flux rate and the mass of solution in the reservoir.

In operation, after the patient or his care giver removes a protective layer from the skin side of the device, the device is adhered to the skin of the patient, e.g., using an applicator so as to maximize proper needle penetration, and the spring is released via a mechanism (not shown) through a start control button or the like, the spring 64 presses on piston 62 applying pressure on the liquid in depot 50, forcing drug through the lumens of the microneedles and into the intradermal compartment of the patient. At the outset the spring is in high compression and exerts a relatively large force on the piston, and a higher flux rate results in rapid establishment of a supra-threshold blood desmopressin concentration. As the spring expands, the force it exerts progressively decreases, and flux rate slows over time, until the desmopressin concentration cannot be sustained, falls below the threshold, and normal urine production commences.

Figure 5:
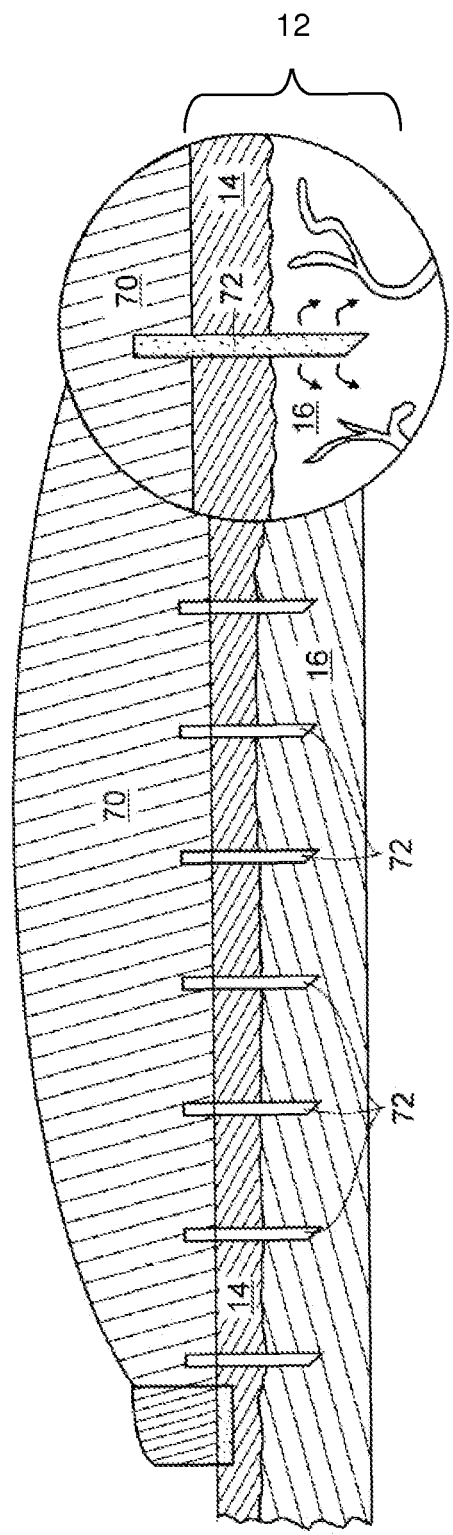
FIG. 5 is a schematic cross-sectional view showing a device of the invention which employs hydraulic pressure to deliver a controlled low dosage of desmopressin into a patient through the skin.

FIG. 5 illustrates still another embodiment of the invention. FIG. 5 shows a passive device designed for intradermal operation featuring dried desmopressin disposed on the surface or within microneedles for sustained release. It comprises a rigid body portion 70 that holds on its bottom surface an array of orthogonally disposed protruding microneedles 72. Like is the embodiment of FIG. 4, these microneedles are dimensioned to penetrate the stratum corneum 14 and to invade the capillary-rich dermis 16 of the subject's skin 12 when the device is applied and adhered to the skin surface. However, in this case dried desmopressin is leached off the tips of the microneedles as it is reconstituted by (dissolved in) body fluids so as to establish the desired desmopressin flux. After the desmopressin is exhausted, the device is removed and discarded.

Figure 6:
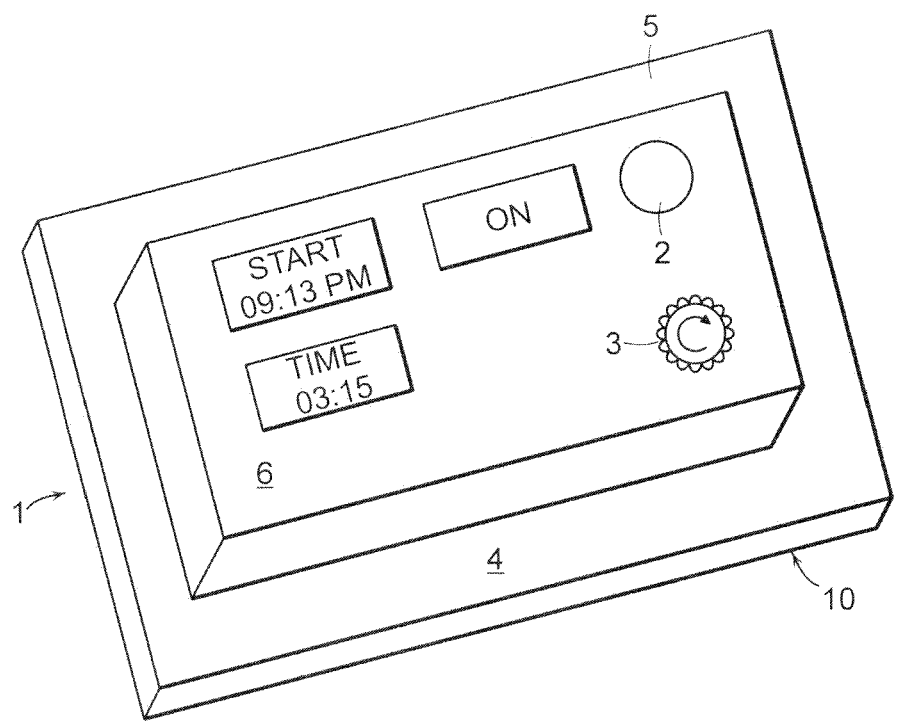
FIG. 6 is a schematic perspective view of the exterior of a battery-powered active device embodying the invention.

FIG. 6 depicts the outside of an embodiment of an active, battery powered, electronically controlled low-dose desmopressin delivery device. The delivery device 1 illustrated in FIG. 6 includes a micro-metering pump which impels drug at rates and at start and stop times controlled by an on board simple microprocessor, by manually operable controls, or both. This type of device is secured to the patient's skin and designed for inducing multiple periods of safe antidiuresis as demanded by the patient. It comprises a proximal surface for application to the skin and a distal structure 5 having a raised portion 6 extending upwardly from a lip 4 along the outer periphery of the device, which houses a desmopressin solution depot and structure for its controlled delivery. A START switch 2, and an interval input 3 initiate and set so the duration of the desmopressin flux. A microprocessor within the device (not shown) may be programmed manually by the user by setting the input 3 to a desired antidiuretic interval (or can be preprogrammed) according to the desired duration and rate of delivery of the drug. The microprocessor may actuate delivery of a solution of the drug in a continuous infusion, optionally at two or more different rates, in a pulsatile manner, or intermittently. For example, the microprocessor can control the delivery to vary the rate during a 3, 5, or 7 hour cycle as is necessary due to the differing requirements of drug dosage during periods of activity, inactivity and sleep, and taking account of the subject's requirements in relation to fluid intake. Optional features such as display windows showing the time the device was started, the duration of the antidiuretic interval, whether the device is currently activated, battery check alarm, etc., also may be provided.

Figure 7:
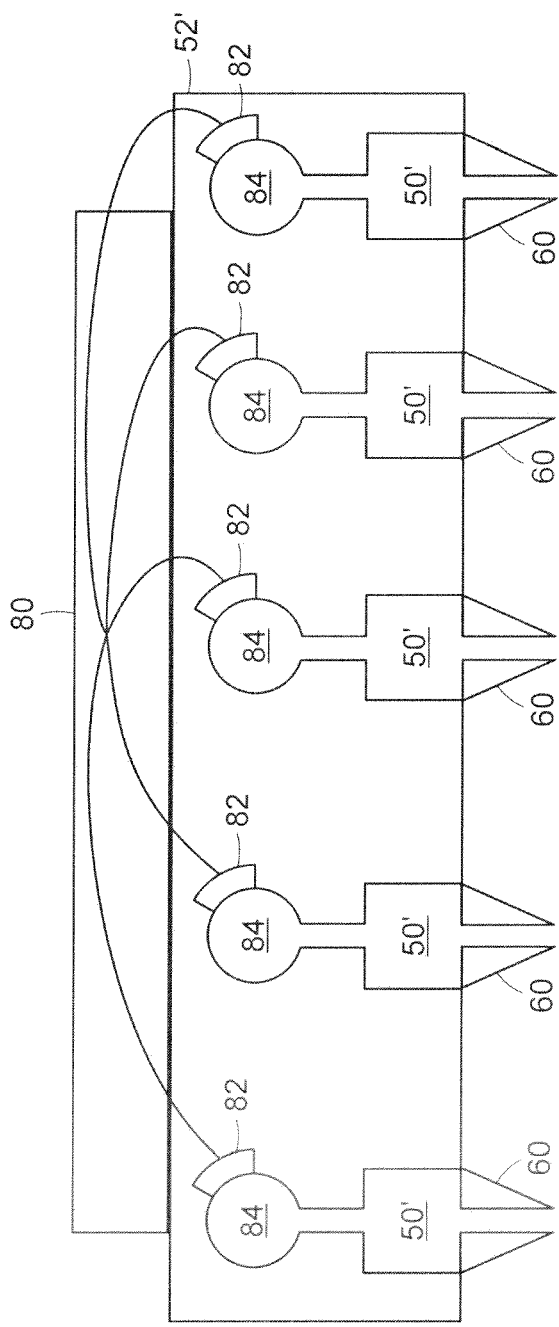
FIG. 7 is a schematic cross-sectional view of a battery-powered device embodying the invention.

FIG. 7 is a schematically depicts a cross-section of one embodiment of an electronically-controlled low dose desmopressin delivery device. The device of FIG. 7 includes several hollow microneedles 60 each protruding from housing 52'. The five hollow microneedles 60 depicted are representative, as several times that number (e.g. fifty, one hundred fifty, or two hundred fifty) may be incorporated into the device. Each hollow microneedle 60 is in fluid communication with one or more depots 50' containing a desmopressin solution. The depots 50' incorporate or are operably connected to activation elements 84 controlled by logic device 80 via electrodes 82. An activation element 84, upon activation, applies a force to expel the desmopressin solution from the attached depot(s) 50' through the hollow microneedle(s) 60. For example, activation element 84 may include a heating element activated by electrode 82. Heat generated by the heating element vaporizes liquid in its vicinity. The generation and expansion of the resulting gas creates an expelling force which may act directly on the desmopressin solution in depot 50', or may be mediated by a membrane, piston, or elastic material. Alternatively, activation element 84 may include one or more chemicals whose reaction is triggered by electrode 82 at activation element 84, generating a gas to create the expelling force against the desmopressin solution in depot 50'.

When the device is applied to the skin, hollow microneedles 60 penetrate the stratum corneum. Logic device 80 activates a selected number (e.g. two) of activation elements 84, each expelling the desmopressin solution in attached depot 50' through hollow microneedle 60 into the skin of the patient to induce a slightly supra-threshold concentration of desmopressin so in the blood. Over time, logic device 80 activates additional activation elements 84 as needed to maintain the desmopressin concentration in the blood based on, for example, a predetermined schedule (e.g. one activation element every five minutes, or every hour), or on feedback from an optional sensor (not shown) detecting sodium ion or desmopressin concentrations in the patient. Desmopressin administration continues until the program in logic device 80 is complete or the device is deactivated or removed by the patient.

EQUIVALENTS

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A device for modulating urine production in a patient, the device comprising:
   (a) a depot containing a solution of desmopressin in a pharmaceutically acceptable carrier;
   (b) an interface member in fluid communication with the depot for application to the skin of a patient;
   (c) means for delivering the desmopressin solution from the depot to the interface member and intradermally or transdermally to the blood of a patient at a flux rate:
      (i) sufficient to establish and maintain a desmopressin concentration in the blood of the patient within the range of about 0.2 to 5 pg/ml and
      (ii) insufficient to induce a desmopressin concentration in the blood of the patient greater than about 5 pg/ml; wherein the desmopressin solution is formulated for transdermal delivery and the interface member comprises a desmopressin solution-permeable membrane for contact with the skin of the patient; and
   wherein the means for delivering comprises pressure exerting means for impelling the solution at a predetermined rate from the depot to the interface member.

2. The device of claim 1, wherein the flux rate is between about 5 and 35 ng/hr (5000 to 35,000 pg/hr).

3. The device of claim 1, wherein the flux rate is between about 10-20 ng/hr.

4. The device of claim 1, wherein the flux rate is between about 5-15 ng/hr.

5. The device of claim 1, wherein the flux rate is about 10 ng/hr.

6. The device of claim 1, wherein the means for delivering the desmopressin solution first establishes a first, higher flux rate to establish a desmopressin concentration in the blood of a patient within the range and a second, lower flux rate to maintain the concentration.

7. The device of claim 6, further comprising a timer for triggering flux rate change.

8. The device of claim 1, wherein the means for delivering comprises a volume of the solution in contact with a surface of the interface member distal to a surface for contact with the skin of the patient, and the desmopressin flux is established by absorptive flow of the solution into the interface member and diffusion from the interface member through the skin of the patient.

9. The device of claim 1, further comprising a desmopressin solution flow switch for initiating or terminating the flow of desmopressin into the blood of the patient.

10. The device of claim 1, wherein said solution has a concentration at the interface member less than about 5.0 µg/mL.

11. A device for modulating urine production in a patient, the device comprising:
   (a) a depot containing a solution of desmopressin in a pharmaceutically acceptable carrier;
   (b) an interface member in fluid communication with the depot for application to the skin of a patient;
   (c) means for delivering the desmopressin solution from the depot to the interface member and intradermally or transdermally to the blood of a patient at a first, higher flux rate:
      (i) sufficient to establish and maintain a desmopressin concentration in the blood of the patient within the range of about 0.2 to 5 pg/ml and
      (ii) insufficient to induce a desmopressin concentration in the blood of the patient greater than about 5 pg/ml; and
   a second, lower flux rate to maintain the desmopressin concentration in the blood of the patient; and
   wherein the desmopressin solution is formulated for transdermal delivery and the interface member comprises a desmopressin solution-permeable membrane for contact with the skin of the patient.

12. The device of claim 11, wherein the first or second flux rate is about 10 ng/hr.

13. The device of claim 11, further comprising a timer for triggering flux rate change.

14. The device of claim 11, wherein the means for delivering comprises pressure exerting means for impelling the solution at a predetermined rate from the depot to the interface member.

15. A device for modulating urine production in a patient, the device comprising:
   (a) a depot containing a solution of desmopressin in a pharmaceutically acceptable carrier;
   (b) an interface member in fluid communication with the depot for application to the skin of a patient;
   (c) means for delivering the desmopressin solution from the depot to the interface member and intradermally or transdermally to the blood of a patient at a first, higher flux rate:
      (i) sufficient to establish and maintain a desmopressin concentration in the blood of the patient within the range of about 0.2 to 5 pg/ml and
      (ii) insufficient to induce a desmopressin concentration in the blood of the patient greater than about 5 pg/ml; and
   a second, lower flux rate to maintain the desmopressin concentration in the blood of the patient, wherein the means for delivering comprises a volume of the solution in contact with a surface of the interface member distal to a surface for contact with the skin of the patient, and the desmopressin flux is established by absorptive flow of the solution into the interface member and diffusion from the interface member through the skin of the patient.

16. The device of claim 11, further comprising as a pressure exerting means a desmopressin solution flow controller for regulating the first or second flux rate of desmopressin into the blood of the patient.

17. The device of claim 11, further comprising a desmopressin solution flow switch for initiating or terminating the flow of desmopressin into the blood of the patient.

18. The device of claim 11, wherein said solution has a concentration at the interface member less than about 5.0 µg/mL.

* * * * *